(12) United States Patent
Buschmann et al.

(10) Patent No.: US 10,653,819 B2
(45) Date of Patent: May 19, 2020

(54) DEVICE FOR REPAIR SURGERY OF CYLINDRICAL ORGANS, PARTICULARLY RUPTURED TENDONS, COMPRISING A THERAPEUTIC AGENT FOR STIMULATING REGROWTH, AND METHOD OF PRODUCING SUCH DEVICE

(71) Applicants: UNIVERSITAET ZUERICH, Zurich (CH); ETH ZURICH, Zurich (CH)

(72) Inventors: Johanna Buschmann, Zurich (CH); Olivera Evrova, Zurich (CH); Viola Vogel, Baden (CH)

(73) Assignees: UNIVERSITAET ZUERICH, Zurich (CH); ETH ZURICH, Zurich (CH)

( * ) Notice: Subject to any disclaimer, the term of this patent is extended or adjusted under 35 U.S.C. 154(b) by 95 days.

(21) Appl. No.: 16/077,051

(22) PCT Filed: Feb. 10, 2017

(86) PCT No.: PCT/EP2017/053072
§ 371 (c)(1),
(2) Date: Aug. 10, 2018

(87) PCT Pub. No.: WO2017/137602
PCT Pub. Date: Aug. 17, 2017

(65) Prior Publication Data
US 2019/0070340 A1 Mar. 7, 2019

(30) Foreign Application Priority Data
Feb. 12, 2016 (EP) ..................................... 16155488

(51) Int. Cl.
*A61F 2/08* (2006.01)
*A61L 27/58* (2006.01)
(Continued)

(52) U.S. Cl.
CPC ............ *A61L 27/58* (2013.01); *A61F 2/0805* (2013.01); *A61L 27/18* (2013.01); *A61L 27/3662* (2013.01);
(Continued)

(58) Field of Classification Search
CPC ........................................................ A61F 2/08
See application file for complete search history.

(56) References Cited

U.S. PATENT DOCUMENTS

2011/0039101 A1   2/2011   Chang et al.

FOREIGN PATENT DOCUMENTS

WO   2013026937 A1   2/2013

*Primary Examiner* — Matthew W Schall
(74) *Attorney, Agent, or Firm* — Agris & Von Natzmer, LLP; Joyce Von Natzmer

(57) ABSTRACT

A device for repair surgery of cylindrical organs, particularly of ruptured tendons, is configured as a tubular sheath (T) made of a mesh of elastic fibers formed by electrospinning a biocompatible and biodegradable polymer. The tubular sheath has a Young elasticity modulus of about 0.1 to about 4 MPa and a strain at break of about 50 to about 1,000%, and it has a first wall surface and a second wall surface substantially parallel thereto, with said first wall surface being comparatively smooth ($W_S$) and said second wall surface being comparatively rough ($W_R$). According to the invention, the elastic fibers comprise first fibers consist of polymer in neat form and second fibers consist of polymer with an admixture of a therapeutic agent for stimulating regrowth processes of a predetermined cylindrical organ. The tubular sheath comprises a first tubular region adjacent to the first wall and a second tubular region adjacent to the second wall, said first tubular region being formed of said first fibers and said second tubular region being formed of said second fibers.

16 Claims, 12 Drawing Sheets

(51) Int. Cl.
*A61L 27/18* (2006.01)
*A61L 27/36* (2006.01)
*A61L 27/54* (2006.01)
*D01D 5/00* (2006.01)

(52) U.S. Cl.
CPC ............ *A61L 27/54* (2013.01); *D01D 5/0007* (2013.01); *A61L 2430/10* (2013.01)

DegraPol®

A

Single Electrospinning

B

Emulsion Electrospinning

C

Release of Fluorescein (FL)

Release of Bovine Serum Albumin (FITC-BSA)

DEVICE FOR REPAIR SURGERY OF CYLINDRICAL ORGANS, PARTICULARLY RUPTURED TENDONS, COMPRISING A THERAPEUTIC AGENT FOR STIMULATING REGROWTH, AND METHOD OF PRODUCING SUCH DEVICE

CROSS-REFERENCE TO RELATED APPLICATIONS

This is the U.S. national stage of International application PCT/EP2017/053072, filed Feb. 10, 2017 designating the United States and claiming priority to EP patent application 16155488.6, filed Feb. 12, 2016.

FIELD OF THE INVENTION

The present invention relates to a device for repair surgery of cylindrical organs, particularly ruptured tendons. Moreover, the invention relates to a method of producing such a device.

BACKGROUND OF THE INVENTION

Tendon ruptures constitute a major part of musculoskeletal injuries, with Achilles tendon ruptures as one of the most frequently ruptured tendons in the human body.[1] Functional loss of the repaired tendons is due to two major drawbacks, (i) adhesion formation to the surrounding tissue, resulting in a reduced range of motion and (ii) insufficient mechanical strength acquired during initial tendon healing, leading to re-rupture.[1] Due to limited tendon vascularity and innervation, the natural healing of the tendon is inefficient[2] and therapeutic repair options include autografts, allografts, xenografts, suture techniques and tendon prostheses.[3]

A regenerative engineering approach addressing the major drawbacks in Achilles tendon rupture, has been explored before by developing a reversibly expandable electrospun polymer tube, made from a biodegradable co-block polymer, a polyester urethane named DegraPol® (DP)[4], see also WO 2013/026937 A1. Electrospun tube made of a newly synthesized type of DP, which is softer and more elastic, surgeon friendly and better suited for tendon rupture repair[4], compared to the already established classic DP[5] has been applied over the wound site after conventional tendon repair. It has been shown that is does not evoke an adverse cellular response and that it significantly minimized peritendinous adhesion formation in a rabbit model.[6] Using this newly synthesized DP for production of reversibly expendable electrospun scaffolds/tubes offers a big advantage over other electrospun polymers like poly(lactide-co-glycolic acid) (PLGA) or poly(caprolactone) (PCL), that exhibit considerably low strain at break.[7]

To address the issue of insufficient strength at the tendon rupture repair site and to further develop the elastic DP tube as an implant for tendon rupture repair, it has been explored as a carrier system for growth factor(s), more specifically platelet-derived growth factor-BB (PDGF-BB). This approach aims to provide a bioactive scaffold that can locally promote and accelerate tendon healing. Administration of biological molecules like growth factors has been proposed and studied in aiding the recapitulation of the native tendon function after injury.[8] More specifically, PDGF-BB has been shown to affect matrix remodeling, increase collagen synthesis and cell proliferation[9], thus its local delivery might also affect the biomechanical strength of the repaired tendons.

SUMMARY OF THE INVENTION

In view of the above, it is an object of the present invention to provide an improved device for repair surgery of cylindrical organs, particularly ruptured tendons.

These objects are achieved by a device for repair surgery of cylindrical organs, particularly ruptured tendons, as defined in claim 1. The device is configured as a tubular sheath (T) made of a mesh of elastic fibers formed by electrospinning at least one biocompatible and biodegradable polymer, said tubular sheath having a Young elasticity modulus of about 0.1 to about 4 MPa and a strain at break of about 50 to about 1,000%, said tubular sheath having a first wall surface and a second wall surface substantially parallel thereto, said first wall surface being comparatively smooth ($W_S$) and said second wall surface being comparatively rough ($W_R$). According to the invention the elastic fibers comprise first fibers consisting of a first one of said polymers in neat form and second fibers consisting of a second one of said polymers with an admixture of a therapeutic agent for stimulating regrowth processes of a given cylindrical organ to which the device shall be applied. The tubular sheath comprises a first tubular region adjacent to said first wall and a second tubular region adjacent to said second wall, said first tubular region being formed of said first fibers and said second tubular region being formed of said second fibers. The dividing region between the first and second tubular regions may comprise a boundary zone containing both types of fibers, i.e. first fibers and second fibers intermingled to each other.

While it is contemplated that the device may be used for repair surgery of a whole variety of cylindrical organs such as nerves, blood vessels and certain muscles in humans or other animals, particularly mammals, it is particularly useful for repair surgery of ruptured tendons in humans. In the present context the term "cylindrical" shall be understood as "having substantially cylindrical symmetry" in line with the fact that human and animal organs do not exhibit perfect cylindricity in the geometrical sense both because of inherent slight irregularities of their shape and variations in cross sectional size, but also because of their deformability.

The term "polymer in neat form" shall be understood as a polymeric material as defined elsewhere without any admixture of the therapeutic agent selected for stimulating regrowth processes in the selected organ. It is not excluded, however, that the first tubular region could contain some other type of therapeutic agents to be delivered in an outwards direction, i.e. to a body region peripherally surrounding the ruptured organ.

The term "polymer with an admixture of a therapeutic agent for stimulating regrowth processes" shall be understood in a broad sense so as to include various types of loading the therapeutic agent onto or into a polymeric fiber.

The terms "biocompatible" and "biodegradable" are generally known in the field of surgery. Synthetic biocompatible and bioresorbable polymers are becoming increasingly popular for surgical applications either as tissue engineered artificial grafts and/or as bioactive carrier devices delivering growth factors (Costa et al. 2006), cytokines and other bioactive substances (Maurus et al. 2006; Corsi et al. 2007; Bullough et al. 2008). Tendon grafts can also be seeded with stem cells improving the early healing process (Chong et al. 2007). The advantage of such polymers is that their mechanical properties as well as their degradation rates can be controlled and adjusted for specific medical applications (Saad et al. 1999; Durselen et al. 2001; Milleret et al. 2009; Sahoo et al. 2010). Moreover, tissue integration can be regulated by porosity and architecture of the material used for grafting (Henry et al. 2009).

The technique of forming a tubular sheath comprising an elastic polymeric fiber mesh by electrospinning is generally known (see, e.g. US 2011/0039101 A1). As the fiber mesh is formed on a cylindrical or conical target with a smooth surface, the resulting sheath has a comparatively smooth surface on its inner wall adjacent the target and a comparatively rough outer surface on its outer wall. For example, the smooth surface will have a dynamic friction coefficient of about 0.85 whereas the rough surface will have a dynamic friction coefficient of about 1.05. As will be explained in more detail further below, this difference in surface roughness can be exploited in repair surgery by first everting the tubular sheath so as to have the rough surface as the inner wall. This allows for firm contact of the sheath with the cylindrical organ to be repaired and reduces the friction between the outer wall and any surrounding tissue, thereby improving mobility of the repaired organ, for example gliding of a tendon in the tendon sheath.

By virtue of its configuration of a double-layered electrospun tube which, when applied on a ruptured organ site, has a comparatively rough bioactive inner layer capable of delivering a therapeutic agent at the repair site and an a comparatively smooth outer layer acting as a physical barrier towards the surrounding tissue, the device of the present invention provides for a substantively improved healing process. When the fiber material of the inner wall slowly decomposes, typically on a time scale of a few weeks, the therapeutic agent contained therein is gradually released and delivered to the repaired organ region.

By having a Young elasticity modulus of about 0.1 to about 4 MPa and a strain at break of about 50 to about 1,000%, the tubular sheath can be readily expanded when being placed on the repaired region and it can subsequently provide a long lasting radially inward directed pressure that contributes to the improved healing process.

The diameter of the tubular sheath will be selected according to the size of the organ to be repaired. In general, it will be chosen to be slightly narrower than the outer diameter of the organ to be repaired, so that the tubular sheath can be applied onto the relevant organ region after slight radial expansion. For the repair of human tendons, the tubular shell will have a diameter in the range of about 1 to about 5 mm.

Advantageous embodiments of the invention are defined in the dependent claims.

It is contemplated that the biocompatible and biodegradable polymers used to form the first fibers and the second fibers, respectively, may be different polymeric species. In particular, the polymer used to form the first fibers, henceforth also called "first polymer", may be selected in order to optimize mechanical properties of the device. In contrast, the polymer used to form the second fibers, henceforth also called "second polymer", may be selected to optimize the release of the therapeutic agent. In a specific embodiment (claim 2), however, the first polymer and the second polymer are one and the same polymeric species. This allows for a simplified production method.

According to an advantageous embodiment (claim 3), at least said second polymer is a biodegradable polyester urethane block copolymer with poly-hydroxy-butyrate as a hard segment and ε-caprolactone as a soft segment. Such polymers are known and can be purchased as DegraPol® from ab medica s.p.a., Italy. Degrapol has been shown to be biocompatible for fibroblasts, osteoblasts and tenocytes in vitro; moreover, it is biodegradable as well as cyto- and hemocompatible (Saad et al. 1998; Sukthankar 1999; Milleret et al. 2009). The degradation rate can be adjusted in the range from a few weeks up to a few years. It is contemplated that different subtypes of the above mentioned polyester urethane block copolymer can be used to form the first and second polymer fibers. Alternatively, the first polymer may be formed of a different polymeric species.

A particularly preferred embodiment (claim 4) involves a selected type of the above mentioned polyester urethane block copolymer, characterized by a soft segment with an average molecular weight of about 900 g/mol to about 1,250 g/mol, a relative content of said soft segment of about 60 to about 75 parts by weight and a relative content of said hard segment of about 40 to about 25 parts by weight. The term "relative content" is used here because, as will be generally known, formation of such block copolymers further requires the addition of an appropriate coupling agent. In the present case, this is an isocyanate coupler. If not specifically mentioned otherwise, average molecular weights reported here are number averaged molecular weights $M_n$, which can be determined e.g. by means of gel permeation chromatography (GPC).

According to a particularly advantageous embodiment (claim 5), the tubular sheath has a Young elasticity modulus of about 0.4 to about 2.5 MPa and a strain at break of about 200 to about 1000% As already pointed out further above, the device of the present invention is generally intended for repair surgery of organs with substantially cylindrical symmetry. This also includes configurations with variable diameter. Therefore, according to one embodiment (claim 6) the tubular sheath is of substantially frustoconical shape, i.e. it has a diameter that monotonously decreases in one axial direction.

Typically, the half-aperture angle, i.e. the angle between the wall surface and the longitudinal axis will be in the range of about 1 to about 10°. However, the useful tubular shapes also include configurations with a nonlinear diameter variation, i.e. having a curved longitudinal section. The specific shape will be selected according to the shape of the organ to be repaired. As will be understood, the manufacture of tubular sheaths with such specific shapes by electrospinning is readily achieved by selecting an appropriately formed deposition target.

According to an advantageous embodiment (claim 7), the second fibers are heterogeneous filaments having included cavities filled with said therapeutic agent. As explained further below, such fibers can be produced by the method of emulsion electrospinning, in which the process is applied to an emulsion of the polymer and an aqueous solution containing the therapeutic agent. Depending on the process parameters, the agent filled cavities will have varying sizes and will be distributed randomly within the fiber. The release of therapeutic agent will begin as soon as there has been sufficient polymer degradation to expose some of the filled cavities.

According to another advantageous embodiment (claim 8), the second fibers are hollow filaments having a central core filled with said therapeutic agent. With such a tubular core-shell architecture, the release of therapeutic agent will begin in a nearly step-like manner once the polymer forming the tube wall has sufficiently degraded.

The second tubular region may form about 5 to about 95 percent of the wall thickness, with the remainder being formed by the first tubular region. In this manner one can optimize the amount of therapeutic agent that is ultimately released by the device and the mechanical reinforcement provided mainly by the first tubular region. According to one embodiment (claim 9), the first tubular region and the second tubular region each form about one half of the sheath's wall thickness.

The device of the present invention is suitable for delivery of a large variety of therapeutic agents, which term shall be interpreted in a broad sense and include any agents that could have a beneficial effect on the healing process after repair surgery. In particular (claim 10), the therapeutic agent can be selected from the group consisting of growth hormones, pharmaceutical agents and growth promoting cells, including stem cells. In a particularly advantageous embodiment (claim 11) the therapeutic agent is platelet-derived growth factor-BB, henceforth also termed "PDGF-BB".

According to another aspect of the invention, there is provided a method of producing a device as defined above, in which method said elastic fibers are formed by solution electrospinning. This technique is generally known. In contrast to melt electrospinning, in which polymer fibers are formed from a melt of the respective polymeric species, solution electrospinning is based on using a solution of the respective polymeric species in a volatile solvent. The solution is driven from a reservoir through a nozzle or needle, after the exit of which the solvent evaporates and a thread of first polymer fibers is formed. To produce the tubular sheath of the present invention, one can start the electrospinning process with a solution of the first polymer, which leads to formation of the first tubular region having a smooth first wall contacting the production target. Subsequently, the process is continued by admitting a solution or emulsion of the second polymer and the therapeutic agent, whereby the second tubular region comprising second polymer fibers is deposited around the first tubular region. Depending on how the transition is made between these two process steps, a dividing region between the first and second tubular regions comprising a boundary zone containing both types of fibers, i.e. first fibers and second fibers intermingled to each other will be produced.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein are shown.

A) CLSM images of screening range of PDGF-BB concentrations (ng ml$^{-1}$) for proliferative effect on Achilles tendon rabbit tenocytes in serum free conditions using EdU proliferation assay. B) CLSM images of screening range of PDGF-BB concentrations (ng ml$^{-1}$) for proliferative effect on Achilles tendon rabbit tenocytes in serum$^+$ conditions using EdU proliferation assay. C) EdU-positive cells [%] for each PDGF-BB concentration in serum free condition. D) EdU-positive cells [%] for each PDGF-BB concentration in serum$^+$ condition. E) Bioactivity of released PDGF-BB from DP scaffolds in serum free condition, expressed in EdU-positive cells [%]. F) Bioactivity of incorporated PDGF-BB on DP scaffolds in serum$^+$ condition, expressed in EdU-positive cells [%]. ( $p<0.01$, * $p<0.001$.) Scale bar: A), B), E) and F) 100 μm.

Figure 9A:
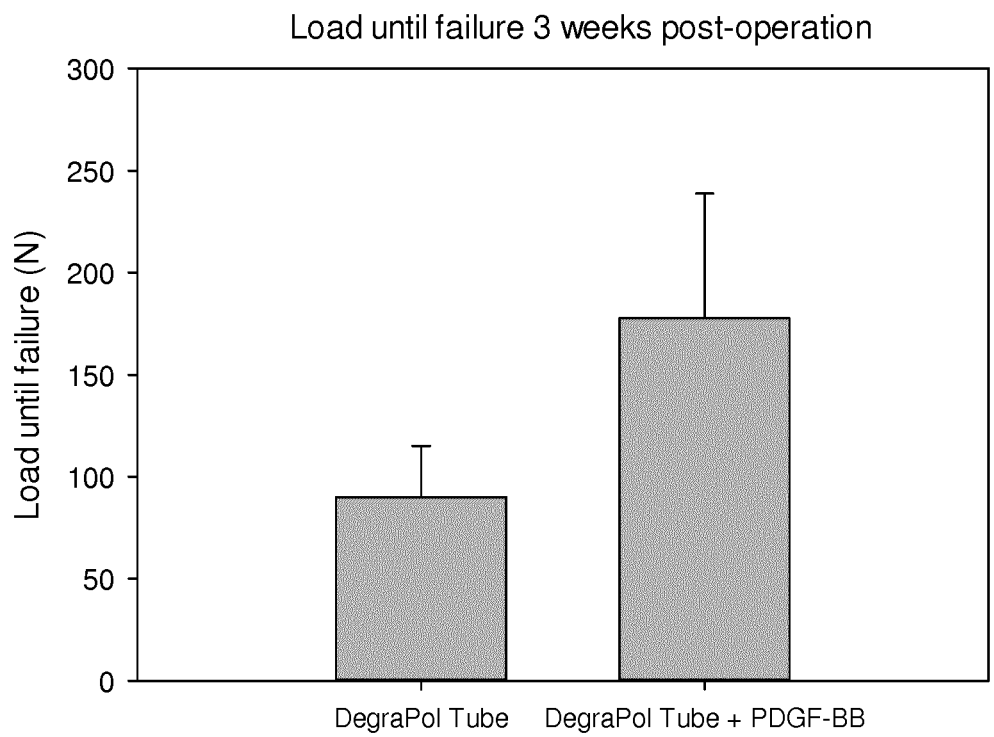
Figure 9B:
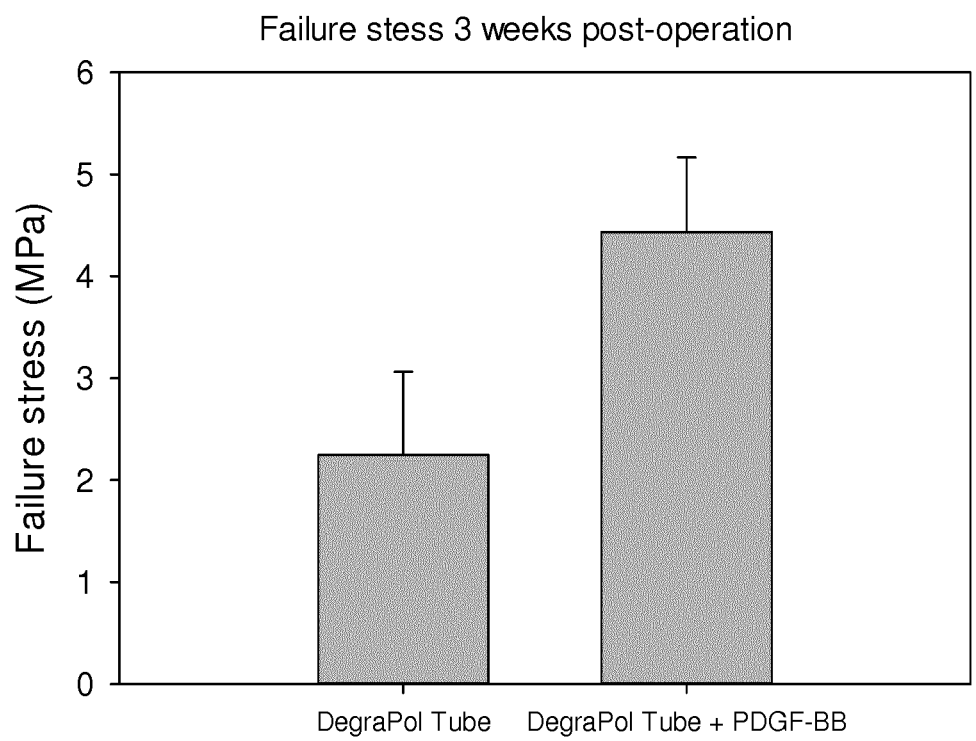

FIG. 9 Biomechanical properties of extracted rabbit Achilles tendons three weeks post-surgery. In both groups, an electrospun DegraPol® tube was implanted around the fully transsected and sutured tendon, however, in one group (denoted by DegraPol Tube+PDGF-BB), the growth factor PDGF-BB was incorporated. As can be concluded, the growth factor affected ultimate failure load as well as ultimate stress of the corresponding specimen: They were higher compared to the tendon treated without PDGF-BB.

FIG. 10 Biomechanical properties of extracted rabbit Achilles tendons three weeks post-surgery. In a first group (left, denoted by "DegraPol Tube"), a DegraPol® tube was implanted around the fully transsected and sutured tendon; in a second group (middle, denoted by "DegraPol Tube+PDGF-BB"), the growth factor PDGF-BB was incorporated in the tube; in a third group (right, denoted by "Control", no tube was applied. Black bars (left side of each group) show data from experiments conducted to test emulsion electrospun tubes whereas grey bars (right side of each group) show data from experiments conducted to test coaxially electrospun tubes. The measured properties were: (a) tendon length in mm, (b) cross sectional area (CSA) in cm$^2$, (c) load until failure in N, (d) failure stress im MPa, (e) stiffness in N/mm, and (f) elastic modulus in MPa.

DETAILED DESCRIPTION OF THE INVENTION

Figure 1:
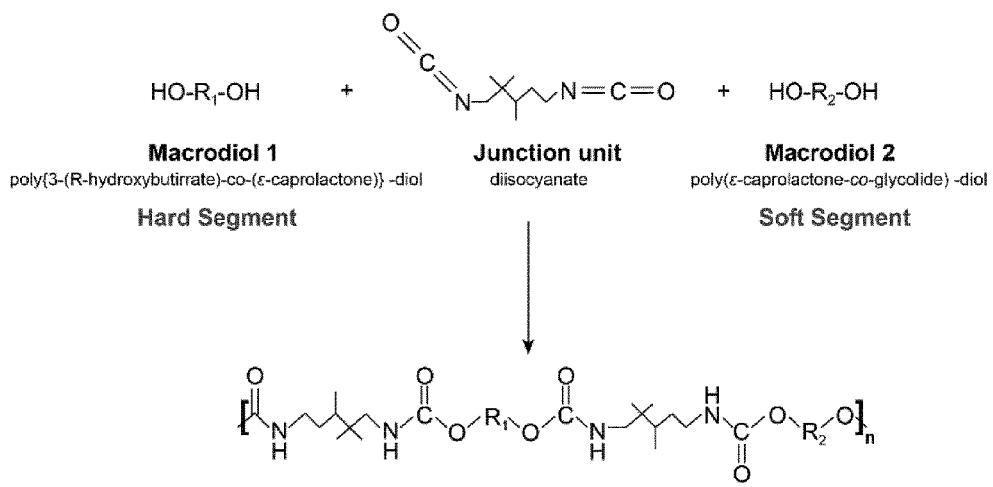
FIG. 1 Single and emulsion electrospinning of DegraPol®. A) Structure of the co-block-polymer DegraPol® consisting of a hard and a soft segment joined by isocynate junction unit. B) During the process of single electrospinning, only simple polymer fibers are obtained. C) Emulsion electrospinning allows for incorporation of biomolecules in an aqueous phase, into the fibers, resulting with either randomly distributed molecules within the fiber (bottom) or core-shell architecture of the fiber (top).
Figure 1:
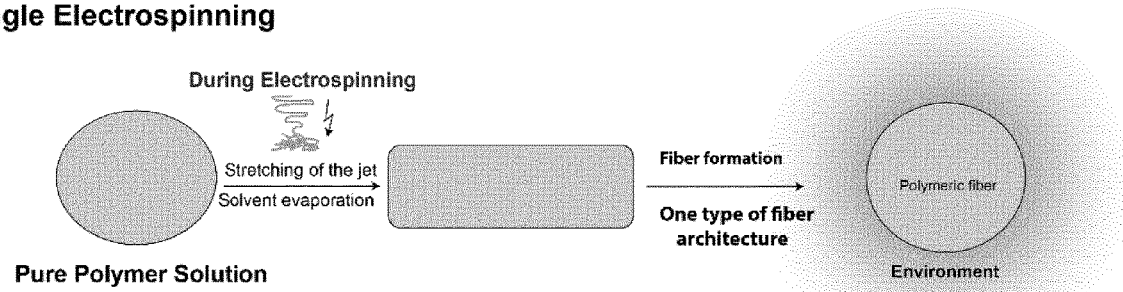
Figure 1:
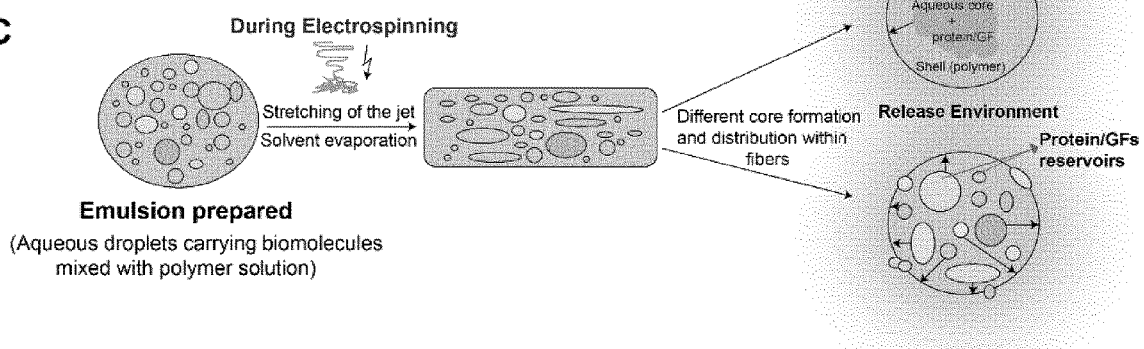
Figure 2:
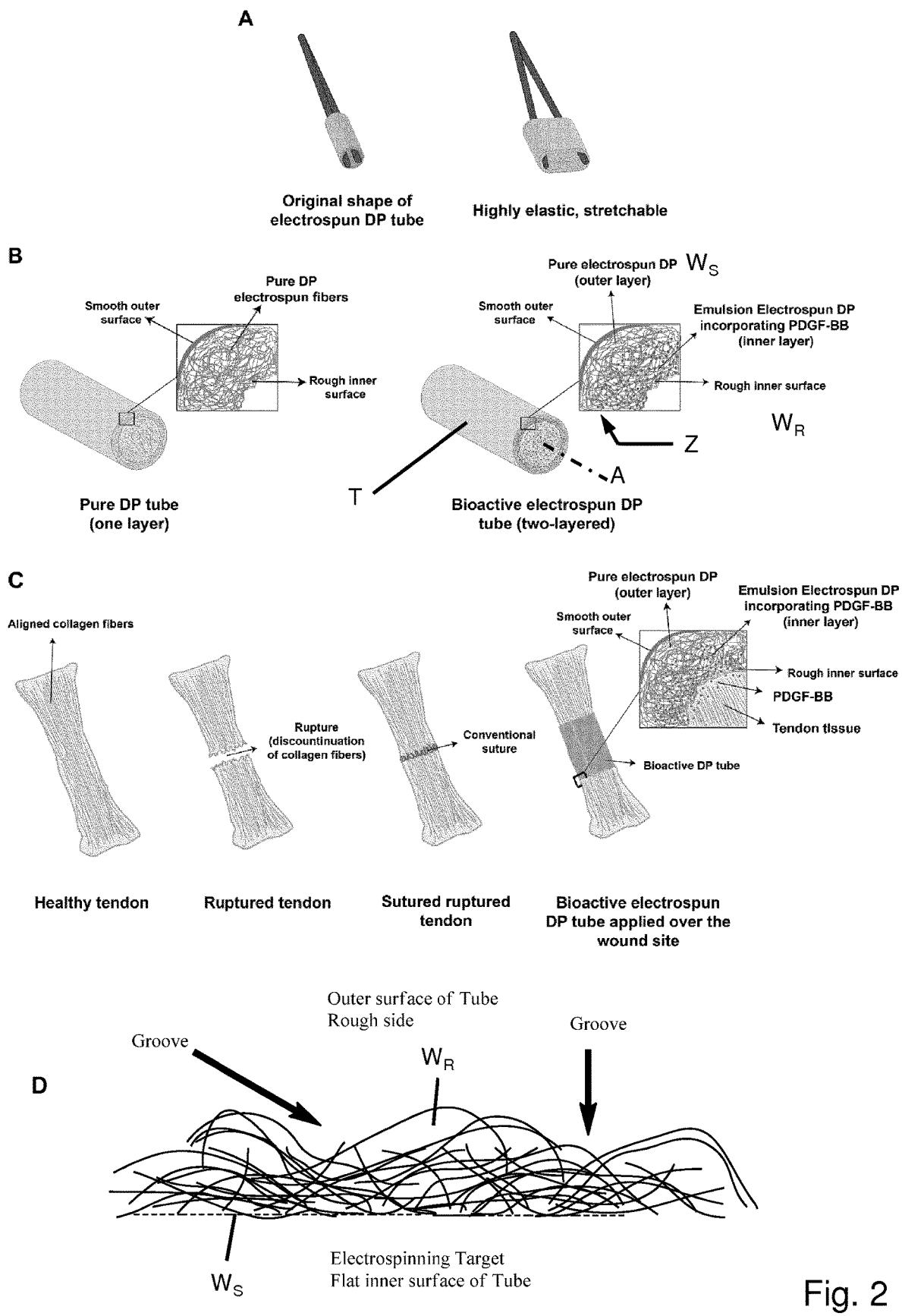
FIG. 2 Schematic overview of the design of the bioactive DegraPol® tube and its anticipated clinical application for tendon repair. A) Reversibly expendable DP tube, made from a new highly elastic DP. B) Design of single electrospun (pure) DP tube (one-layer) and bioactive electrospun DP tube (two-layered), incorporating PDGF-BB in the emulsion electrospun layer. C) Application of the bioactive DP tube over a conventionally sutured ruptured site of a tendon, delivering PDGF-BB at the wound site. D) Enlarged schematic cross-sectional view of bioactive DegraPol® tube with flat first wall surface (bottom) and rough second wall surface (top) with groove-type features.

The device for repair surgery of cylindrical organs, particularly of ruptured tendons, is shown in FIGS. 1 and 2. It is configured as a tubular sheath (T) made of a mesh of elastic fibers formed by electrospinning a biocompatible and biodegradable polymer. The tubular sheath T is approximately cylindrically shaped along a longitudinal axis A and has a first wall surface, which in the example shown in FIG. 2 is the outer tube surface, and a second wall surface substantially parallel thereto, which in the example shown is the inner tube surface. The configuration shown in FIGS. 2A to 2C is the one to be used for the intended surgical application. This configuration is obtained from a freshly produced electrospun tubular sheath, as shown in FIG. 2D, by everting the same, i.e. by switching the inner and outer side thereof. The first, outer wall surface is comparatively smooth ($W_S$) whereas the second, inner wall surface is comparatively rough ($W_R$), thus allowing good adhesion to the ruptured tendon surface. A first tubular region adjacent to the first, outer wall surface is formed of first fibers consisting of the polymer in neat form. A second tubular region adjacent to the second, inner wall surface is formed of second fibers consisting of the polymer with an admixture of a therapeutic agent for stimulating tendon regrowth processes. The tubular sheath as a whole has a Young elasticity modulus of about 0.1 to about 4 MPa and a strain at break of about 50 to about 1,000%.

As shown in FIG. 2B at the right hand side, the boundary region Z denoted with an arrow is not necessarily a sharp transition between the two types of fibers. Depending on how the electrospinning process is carried out, there may be a gradual transition between the two fiber types if the polymer solution in the reservoir of the electrospinning device is gradually changed from a solution of the neat polymer to a solution also containing the therapeutic agent.

Example 1

Several electrospinning methods for production of bioactive scaffolds include physical adsorption of biomolecules onto scaffolds, electrospinning of emulsions that contain the biomolecules of interest, i.e. emulsion electrospinning or coaxial electrospinning, thus creating an external polymer shell filled with aqueous core carrying biomolecules.[10] Major difficulties using these different methods for biomolecule incorporation are achieving controlled release profiles of the molecules and maintaining their bioactivity. Among these, emulsion electrospinning at least offers easy incorporation of molecules in the scaffold, with a more sustained release profile, compared to a burst release exhibited with physical adsorption methods.[11] Thus, for production of bioactive DP scaffolds emulsion electrospinning was used. Successful incorporation of lysozyme, Rhodamine B, bovine serum albumin (BSA) and some growth factors (NGF and PDGF-BB) into PLGA, PCL and PLLA polymer fibers by emulsion electrospinning has been reported.[12] However, no previous research has been done exploiting DP as a drug delivery system, thus careful morphological and mechanical characterization of the produced scaffolds is necessary to determine whether changes in scaffold production and design affect the scaffold's mechanical and delivery device properties.

The goals of this study were (i) detailed investigation of the impact of electrospinning parameters (voltage, flow rate, weight % of polymer solution) on the morphology (fiber diameter) of the new DP scaffolds; (ii) comparison of pure and emulsion electrospun DP tubes in terms of morphological and mechanical properties; (iii) characterization of DP scaffolds as delivery devices in terms of release kinetics of two model compounds (fluorescein (FL) and fluorescein isothiocyanate-conjugated bovine serum albumin (FITC-BSA)), as well as PDGF-BB, the molecule of interest and (iv) assessing PDGF-BB bioactivity and effect upon release on rabbit tenocytes in in vitro conditions.

EXPERIMENTAL SECTION

Incorporation of Fluorescein and FITC-BSA in DP Polymer Solutions:

DegraPol® (Ab medica, Italy) polymer solutions with 8, 10, 12, 14 or 16 wt % were prepared by dissolving the polymer overnight at room temperature in a mixture of chloroform/HFP (80:20 w/w) (Sigma). For emulsion preparation, fluorescein ($M_w$=376.27 g mol$^{-1}$, Polysciences, Inc., USA) was dissolved in MilliQ water at 5 mg mL$^{-1}$ and FITC-BSA (Sigma) was dissolved in 10 mM Tris-HCl buffer (pH=7.4) at a concentration of 5 mg mL$^{-1}$, each representing the aqueous phase of the emulsion. Water-in-oil emulsions were prepared by drop-wise addition of 200 μL of aqueous phase to the polymer solution while stirring at 500 rpm for 2 minutes. Afterwards the mixtures were sonicated using a probe ultrasonicator (Sonopuls HD 2070, Bandelin, Germany) for 2 minutes at 50% amplitude. All the procedure was done immediately prior to electrospinning. For emulsion characterization prior to electrospinning, few drops of emulsions of different wt % DP polymer solutions and FITC-BSA were mounted on a glass slide and observed under fluorescence microscope (Zeiss Axiovert 200M; Carl Zeiss, Germany). Images were analyzed for average diameter and circularity of emulsion droplets and presented as mean±standard deviations (n=3). Circularity ($4\pi \times$[area]/[perimeter]$^2$) ranges from 0 (infinitely elongated polygon) to 1 (perfect circle).

Incorporation of PDGF-BB in DP Polymer Solution:

Recombinant human PDGF-BB (PeproTech) was diluted in 0.1% BSA in DI water at a concentration of 40 µg mL$^{-1}$. 200 µl of this, containing a total of 8 µg PDGF-BB, were added drop-wise to 5 g of DP polymer solution, under stirring for 2 minutes at 500 rpm. Afterwards the mixture was sonicated with a probe ultrasonicator for 2 minutes at 50% amplitude. Immediately afterwards the emulsion was used for electrospinning.

Scaffold Production by Electrospinning:

In-house assembled electrospinning device was used, consisting of a spinning head with a blunt end made of stainless steel tube (1 mm inner diameter and 0.3 mm wall thickness, Angst & Pfister AG, Zürich, Switzerland), a DC high voltage supply (Glassman High Voltage Inc., High Bridge, N.J., USA), hollow cylindrical aluminum mandrel as a collector and a syringe pump (SP210cZ, WPI, Germany). The DP polymer solutions or emulsions created were loaded in 2 mL syringe (B. Braun Melsungen AG, Germany) and pumped into the spinning head. The electrospinning conditions were varied by changing the concentration of polymer in the solution (8, 10, 12, 14 and 16 wt %), the flow rate (0.5-3 ml h$^{-1}$) used and the voltage (10-17.5 kV) applied between the spinning head and the collector. The distance between the spinning needle and the collector (working distance) was kept constant at 15 cm. The process was done at room temperature (22-23° C.) and 35% humidity. For DP tube production, same electrospinning device was used, where a cylindrical rotating aluminum mandrel (length: 200 mm, diameter: 4 mm) was used as a collector. Pure or emulsion DP polymer solutions were used for DP tube production, using electrospinning parameters of 11-12.5 kV, 1 ml h$^{-1}$ flow rate and 20 cm distance from the collector, under 35% humidity and room temperature. In addition, the spinning head through which the polymer solution was ejected was moving left and right in a range of 5 cm to facilitate equal deposition of fibers on the rotating collector. Spun tubes were removed from the collector with 50% ethanol and washed with water and dried under vacuum at room temperature.

PDGF-BB Adsorption on DP Scaffolds:

PDGF-BB was physically adsorbed on pure DP scaffolds. Electrospun scaffolds were cut into 1.5 cm×1.5 cm pieces and placed in low-binding micro tubes (Sarstedt). 1 mL of 300 ng mL$^{-1}$ PDGF-BB (in 0.1% BSA in 1×PBS) was added to each tube and incubated with the scaffolds for 24 hours at 4° C. Afterwards, the scaffolds were rinsed in distilled water and used for further experiments.

Scanning Electron Microscopy (SEM):

Electrospun scaffolds were dried in vacuum overnight and then samples were mounted on metal stubs with conductive double-sided tape. Samples were sputter coated (SCD500, Bal-tec) with platinum in order to obtain 10 nm coating and then examined by SEM (Zeiss SUPRA 50 VP, Zeiss, Cambridge, UK) at an accelerating voltage of 5 kV. Fiber diameters of each sample were measured using SEM images and the image analysis software platform Fiji. First a diagonal line was drawn on the image, and the fiber diameter of the fibers was measured perpendicular to the fiber length at the points where the diagonal line crossed the fibers. The measurement was done manually with the measurement tool in Fiji, after calibration with the scale bar of the microscope image. Three images of each scaffold were analyzed, with an average of 30 counts per scaffold (n=10/image). Fiber diameters are given as averages±standard deviations.

Confocal Laser Scanning Microscopy (CLSM):

Emulsion electrospun DegraPol® scaffolds with incorporated fluorescein or FITC-BSA were analyzed with confocal microscopy in order to visualize the presence and distribution of the molecules within the electrospun fibers. A thin layer of different emulsion electrospun DP fibers was collected on glass coverslips and then observed by CLSM (SP5, Leica Microsystems, Wetzlar, Germany). The excitation wavelength for both fluorescein and FITC-BSA was 488 nm, and images were taken with 63x/1.4 NA objective.

Mechanical Testing of Scaffolds:

The mechanical properties of pure and emulsion electrospun DP tubes (8, 10 and 12 wt % DP) were obtained from stress/strain curves measured using a uniaxial load test machine (Instron tensile tester, High Wycombe, Buck, UK: model 5864) equipped with 10 N load cell. The mechanical properties of the tubes were measured in two directions, the axial and transverse direction of the tube. Standard dog-bone shaped samples with a testing region of 12×2 mm$^2$ and thickness range of 500-800 m were punched out from the tubes in the longitudinal direction and an elongation rate of 12 mm/min was applied until failure. Rectangular samples with a testing region 12×2 mm$^2$ were cut in the transverse direction and elongation rate of 12 mm/min was applied until failure. The Young's modulus [MPa], strain at break (%) and tensile strength [MPa] were determined for every direction in every condition (n=3).

In Vitro Release of Fluorescein, FITC-BSA and PDGF-BB from DP Scaffolds:

Emulsion electrospun scaffolds incorporating fluorescein or FITC-BSA were cut in pieces (20-30 mg) and shortly wetted in 50% ethanol and rinsed in MilliQ water. The scaffolds (n=9) were placed in micro test tubes and 1 mL of release medium was added. The release of fluorescein was performed in MilliQ water, while that of FITC-BSA was performed in 10 mM Tris-HCl buffer (pH 7.4). Samples were incubated at 37° C. and 5% CO$_2$ under mild shaking. At each respective time point (t=12, 24, 48, 72, 120, 168, 336 hours) samples were taken out and placed in new micro test tubes and 1 mL of fresh release medium was added. The concentration of fluorescein or FITC-BSA in the release medium was determined by measuring the fluorescence of each sample by a fluorescence plate reader (Infinite®200, Tecan, Switzerland) at 485 nm excitation and 540 nm emission. The concentration of the samples was calculated based on standard curves of known concentration of fluorescein and FITC-BSA in each respective release medium used. At the end of the release time period, extraction of not released molecules from the DP scaffolds was performed. The extraction of the scaffolds was done by dissolving the scaffold in 1 mL of chloroform by shaking at 800 rpm at room temperature, followed by addition of 1 mL of aqueous phase (MilliQ water for fluorescein and 10 mM Tris-HCl buffer for FITC-BSA). The two phases were mixed together overnight and afterwards the samples were centrifuged at 10 000 rcf for 30 minutes. The concentration of fluorescein or FITC-BSA was measured in the supernatant with fluorescence plate reader. The total loaded amount of molecule was the determined extracted amount added to the cumulative release at the end time point. The results are presented as cumulative release [%] as function of time and calculated by Equation (1):

$$\text{Cumulative release } [\%] = \left(\frac{M_r}{M_t}\right) \times 100 \quad (1)$$

where $M_r$ is the amount of released molecule at time t and $M_t$ is the total released amount of molecule from the scaffold at the end time point plus the extracted leftover amount of molecule from the scaffold upon release.

Emulsion electrospun DP scaffolds incorporating PDGF-BB were cut in pieces (20-30 mg), placed in low-binding micro tubes (Sarstedt) and 500 μL of 0.1% BSA in 1×PBS were added as release medium. Samples (n=9) were incubated at 37° C. and 5% $CO_2$ under mild shaking. At each respective time point (t=1, 2, 3, 5, 7, 10, 14, 21 and 30 days) samples were taken out and placed in new micro test tubes and 500 μL of fresh medium were added. Release samples were stored at −20° C. until further quantification and bioactivity assays. Human recombinant PDGF-BB was quantified with PDGF-BB ELISA kit (PeproTech) according to manufacturer's protocol and samples were measured with an absorbance plate reader (Infinite®200, Tecan, Switzerland) at 405 nm and correction set at 650 nm. Release of PDGF-BB is represented as cumulative release over time in pg ml$^{-1}$, cumulative release [%] based on theoretical loading or normalized to the weight of DP scaffolds as pg mg$^{-1}$ of DP scaffold.

PDGF-BB Detection on Electrospun DP Scaffolds:

Physically adsorbed PDGF-BB on pure DP scaffolds or incorporated on emulsion electrospun DP scaffolds was detected by immunostaining. Samples were washed with 1×PBS, blocked with 3% BSA (Sigma) in 1×PBS for 1 hour at room temperature, washed 3× with 1×PBS and incubated with 1 μg ml$^{-1}$ rabbit anti-PDGF-BB polyclonal antibody (PeproTech) overnight at 4° C. The samples were then washed 3× with 1×PBS and incubated with 10 μg ml$^{-1}$ AlexaFluor®488 goat anti-rabbit (Life Technologies) for 1 hour at room temperature. Afterwards, samples were washed 3× with 1×PBS and mounted with mounting medium (DAKO) and imaged with confocal microscope (SP5, Leica Microsystems, Wetzlar, Germany). 408 excitation/455 emission was used for autofluorescence of the DP fibers and 498 excitation/519 emission for secondary antibody visualization. For negative control, scaffolds were incubated with only secondary antibody in the presence of PDGF-BB or with primary and secondary antibodies in the absence of PDGF-BB to detect any non-specific binding of the antibodies to the scaffolds.

Cell Culture:

Rabbit tenocytes were isolated from Achilles tendons of New Zealand White rabbits. Briefly, Achilles tendons were cut out and washed with DPBS (Biowest) with 200 μg mL$^{-1}$ gentamycin (Biowest) and 2.5 μg mL$^{-1}$ amphotericin B (Biowest). Small pieces from the central part of the tendons were cut with a scalpel, put in digestion solution (Ham's F12 (Biowest), 200 gentamycin, 2.5 μg ml$^{-1}$ amphotericin B and 3 mg ml$^{-1}$ collagenase II (147 U mg$^{-1}$, PAN Biotech) and left to react between 12 and 18 hours, at 37° C. and 5% $CO_2$, without shaking. The samples were centrifuged at 400 g for 5 minutes. The pellet was resuspended and added directly to 75 cm$^2$ tissue culture flask with 12 ml of culture medium (Ham's F12, 10% FBS (Biowest) and 50 μg mL$^{-1}$ gentamycin). After 24 hours, the adherent cells were 3× washed with DPBS and fresh 25 ml culture medium were added. In 4 to 5 days, tenocytes migrated out and formed monolayer and were cryopreserved before use. Cryopreserved rabbit tenocytes were thawed and resuspended in culture medium (Ham's F12 with 10% FBS and 1% Penicillin/Streptomycin (P/S) (Life Technologies)). Tenocytes between passages 1 and 4 were used for all experiments.

In Vitro Bioactivity Assays:

The effect of PDGF-BB on rabbit tenocytes was tested by increase in cell proliferation assessed by Click-iT EdU proliferation kit (Life Technologies). The proliferative effect was studied in serum$^+$ (Ham's F12 with 10% FBS and 1% P/S) and serum free (Ham's F12, 1×RPMI vitamins solution (Sigma), 1× non-essential amino acids solution (Life Technology) and 1% P/S) culture medium and PDGF-BB concentrations of 1-50 ng mL$^{-1}$ were tested. Cells were seeded in 8-well μ slides, ibiTreat (Ibidi) at 4×10$^4$ cells mL$^{-1}$ (300 μL per well) in serum free medium. Cells were cultured in these conditions for serum starvation synchronization with daily change of serum free medium. After 3 days, different PDGF-BB concentrations in serum free or serum$^+$ medium, respectively (1, 3, 5, 10, 25, 50 ng mL-1 for serum free condition and 10, 25, 50 ng mL$^{-1}$ for serum$^+$ condition), together with 10 μM 5-ethynyl-2'-deoxyuridine (EdU) were added and incubated for 24 hours at 37° C. and 5% $CO_2$. Cells were then fixed, permeabilized and EdU stained according to the kit's protocol. Cell nuclei were stained with 5 μg mL$^{-1}$ 4'6-diamidino-2-phenylindole dilactate (DAPI) for 10 minutes. Samples were imaged with confocal microscope and 30 random images were taken per sample (n=6). Results are expressed as EdU-positive cells [%]±standard deviations.

For determining of the bioactivity of the released PDGF-BB from the emulsion electrospun DP scaffolds, the aliquots from each release experiment respectively were pooled together and concentrated using 10K Amicon Ultra-0.5 Centrifugal Filter units (EMD Millipore) according to manufacturer's protocol. The concentrated samples were diluted in serum free medium containing 10 μM EdU, added to serum starved synchronized tenocytes and incubated for 24 hours. Afterwards, the cells were fixed, permeabilized and EdU stained and the percentage of EdU-positive cells was determined.

For determining PDGF-BB bioactivity directly on DP scaffolds, tenocyte proliferation on pure DP, emulsion electrospun DP with PDGF-BB, empty emulsion electrospun DP without PDGF-BB (Emulsion DP+BSA) and pure DP with physically adsorbed PDGF-BB was studied. Scaffolds (1.5× 1.5 cm) were placed in 24-well tissue culture plates and UV-sterilized for 30 minutes. Scaffolds were 1× washed with culture medium and tenocytes (1×10$^5$ cells/scaffold) were seeded in serum$^+$ medium. After overnight culturing of the cells on the scaffolds, the medium was replaced with a fresh one containing 10 μM EdU and samples were incubated for additional 24 hours. The samples were fixed, permeabilized and EdU stained according to the kit's protocol. Scaffolds were mounted on microscope slides with mounting medium (DAKO) and imaged with confocal microscope. 20 random images were taken per scaffold (n=8) and the percentage of EdU-positive cells was determined for each sample.

Statistics:

Data was analyzed with Origin (OriginLab, Northampton, Mass.). Values are expressed as means±standard deviation. One-way analysis of variance (one-way ANOVA) was performed to test the differences between groups in all the experiments, using comparison post-hoc test for significance. p values of less than 0.05 were considered statistically significant results and are indicated with an asterisk within graphs (*p<0.05, p<0.01, *p<0.001).

Results and Discussion

Bioactive DP Scaffold Design

To produce bioactive DP scaffolds that can release PDGF-BB and promote the healing process of tendon rupture repair, we used a newly synthesized, highly elastic type of DP (FIG. 1A). Being slightly different from the standard single electrospinning (FIG. 1B), emulsion electrospinning (FIG. 1C) was chosen as a method for incorporation of biomolecules inside DP electrospun fibers. This new type of DP allows for production of extendable, elastic electrospun tubes that can be pulled over an injured tendon (FIG. 2A). These elastic tubes are surgeon-friendly and easily applicable in clinical settings. Similar to previously tested pure DP scaffold[4] (FIG. 2B), the bioactive DP scaffold was designed to be in the form of a two-layered tube, having a rough electrospun inner layer delivering PDGF-BB at the site of injury and a smooth outer layer, consisting of only pure electrospun DP (FIG. 2B). This DP tube is intended to be applied over the wound of conventionally sutured ruptured tendon (FIG. 2C).[4] Having two-layered tube will allow local delivery of PDGF-BB at the site of injury, however, having a protective layer of pure DP on the outside should limit diffusion of PDGF-BB to the surrounding tissue causing cell migratory effect[13] and not desired adhesion formation.[6]

Morphology and Physical Properties of Emulsion Electrospun DP Scaffolds

As previously not used in emulsion electrospinning and not explored as a drug delivery device, several characterizations of emulsion electrospun DP scaffolds were performed in terms of wt % of DP solution to be used, initial emulsion formation and morphology of obtained scaffolds.

Figure 3:
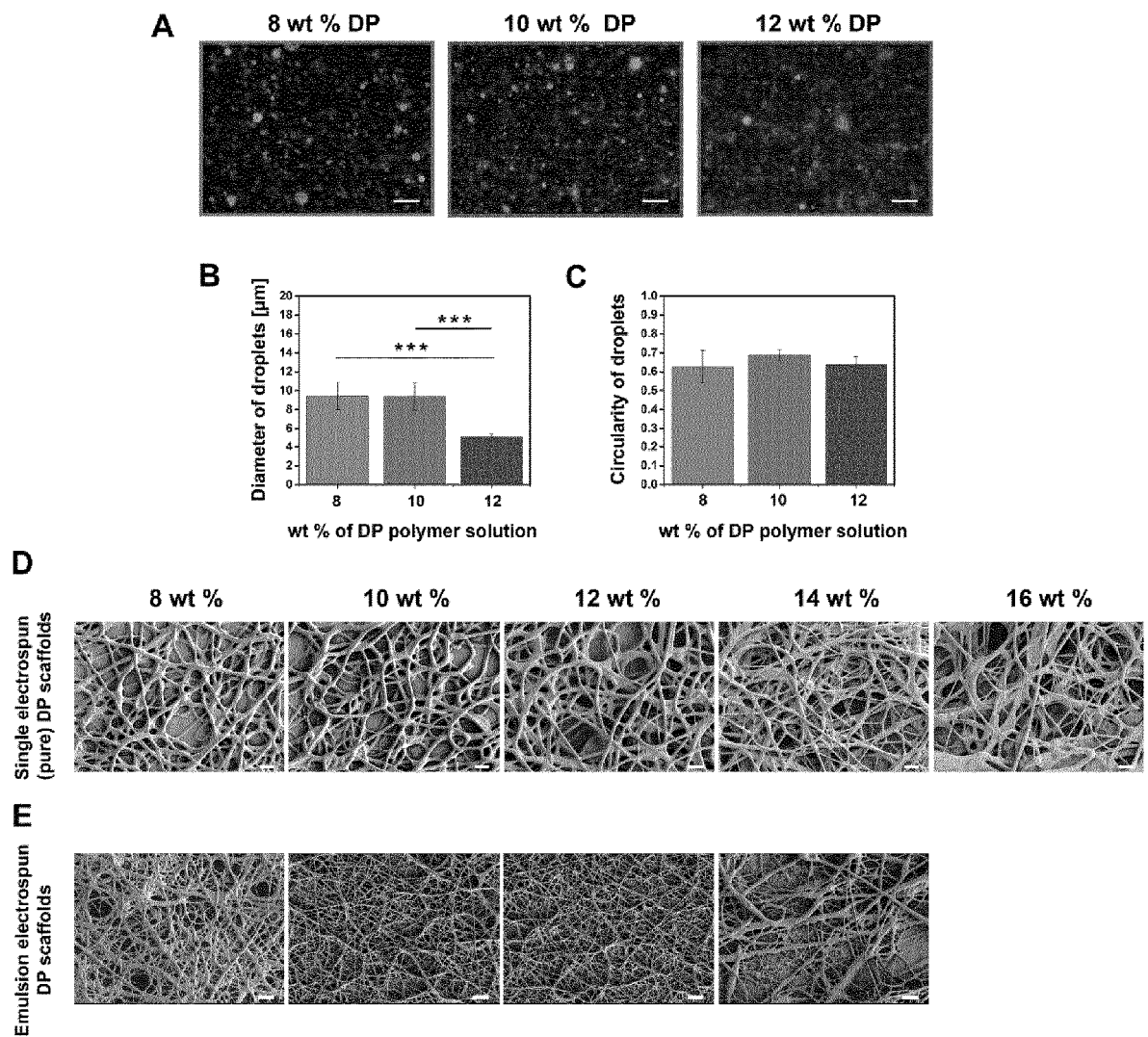
FIG. 3 Characterization of polymer emulsions and scaffolds produced with different wt % of DegraPol®.
A) Fluorescence microscopy images of 8, 10 and 12 wt % DP emulsions with FITC-BSA dissolved in Tris-buffer (pH 7.4) as aqueous phase, prepared before electrospinning. B) Average diameter [m] of droplets and C) average circularity of droplets in each DP-emulsion prepared. D) SEM micrographs of resulting single electrospun DP fibers from only polymer solution (pure DP). E) SEM micrographs of resulting emulsion electrospun DP fibers, at different wt % of DP polymer in the polymer solution used for electrospinning. (***$p<0.001$.) Scale bars: A), D) and E) 20 μm.

Water-in-oil emulsions were prepared, whereby the organic phase consisted of DP polymer solutions (8, 10, 12 wt %), while the aqueous phase contained FITC-BSA in Tris-buffer. Fluorescence microscopy revealed that these emulsions were homogenous in appearance when using 8-12 wt % DP polymer solutions (FIG. 3A). 8 wt % and 10 wt % emulsions had droplets with a diameter of 9.41±1.45 µm and 9.37±0.68 µm, while 12 wt % emulsions experienced a significant decrease in the diameter of the droplets down to 5.05±0.35 µm, thus resulting in more fine emulsions (FIG. 3B). Average circularities of the droplets in each emulsion did not show significant differences between conditions and were 0.65±0.03 on average (FIG. 3C). Classification after Pal et al., defines emulsions with droplet side of 4-12 µm as fine and 25-30 µm as coarse.[14] Thus, the DP emulsions used can be classified as fine emulsions, with droplet size of 5-10 µm and without big phase separations. This suggests that a 0.4% of aqueous phase content is well suited for the preparation of DP emulsions.

The effect of wt % of the DP polymer solution on the fiber morphology of pure and emulsion electrospun DP scaffolds was compared using SEM imaging (FIGS. 3D and E). Proper fiber formation with pure DP solution was possible in the range of 8-12 wt % DP (FIG. 3D). Higher wt % of DP increased the viscosity of the polymer solution, resulting in blob on the fibers, inhomogeneity and increased fiber fusion. For emulsion electrospinning with DP, higher than 14 wt % polymer solutions did not allow for proper emulsion formation and jet formation during the electrospinning process. Emulsion electrospun DP fibers showed the anticipated smooth fiber surfaces, without blobs visible on the fibers, with 14 wt % DP emulsion electrospun scaffolds having high inhomogeneity (FIG. 3E). More viscous polymer solutions require more time and voltage during the electrospinning process for jet stretching and beads and blobs on the fibers can be present due to difficulties in proper jet formation.[15]

The porosity of DP scaffolds produced with single or emulsion electrospinning was gravimetrically determined and compared between 8, 10 and 12 wt % DP. The scaffold porosity for different wt % of DP single electrospun scaffold ranged from 68.35±3.07%, 66.33±5.58% to 63.43±1.96% for 8, 10 and 12 wt % DP scaffolds respectively, without significant differences between them (Figure S1A). For emulsion electrospun DP scaffolds, the porosity ranged from 76.11±2.26%, 74.42±3.45 to 71.33±3.22 for 8, 10 and 12 wt % respectively (Figure S1A). Emulsion electrospun DP scaffolds exhibited significant increase in scaffold porosity when compared to each of the respective wt % of only DP electrospun scaffolds.

In addition the hydrophilicity of the scaffolds was determined by measuring the water contact angle for each sample. Both pure and emulsion electrospun scaffolds (with FITC-BSA incorporated) are hydrophobic after the electrospinning, with static water contact angles from 104.61±1.49 to 124.86±2.87 (Figure S1B).

Effect of Electrospinning Parameters on DP Fiber Diameter

Figure 4:
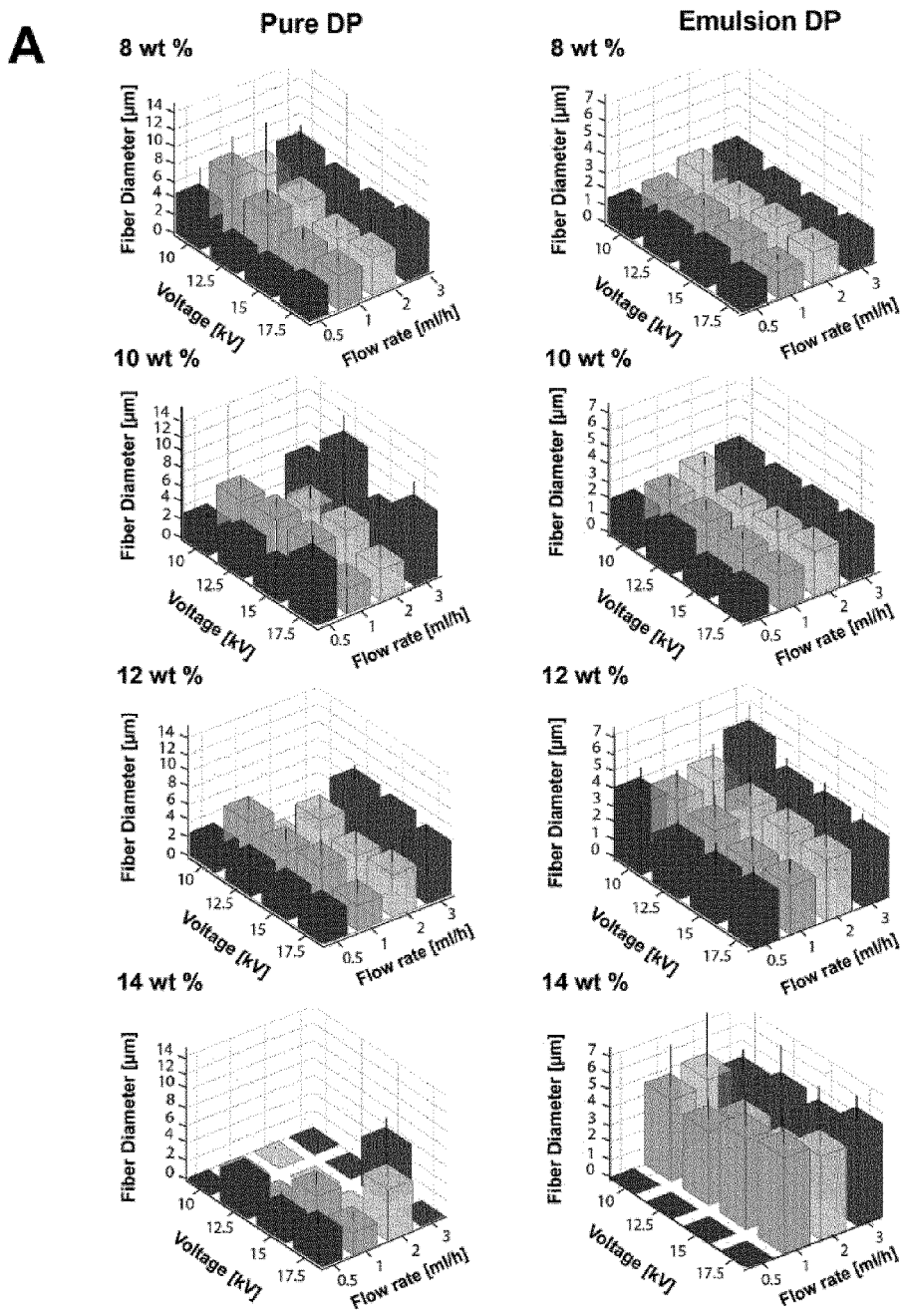
FIG. 4 Effect of emulsion electrospinning and electrospinning parameters on fiber diameter of DegraPol® fibres. A) Effect of different electrospinning parameters (flow rate [ml h$^{-1}$], voltage [kV]) on fiber diameter of single and emulsion electrospun DP fibers, using different wt % of DP polymer solution. B) Fiber diameter as a function of different wt % of DP during single and emulsion electrospinning. (*$p<0.05$, ***$p<0.001$.)
Figure 4:
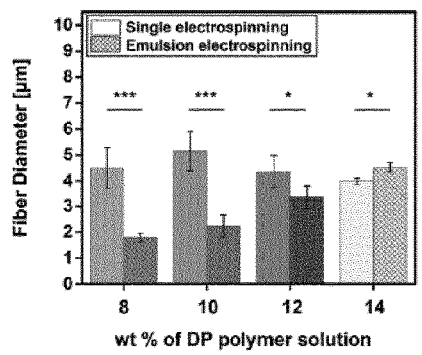

Different electrospinning parameters (voltage, flow rate, wt % of polymer solution, working distance) can affect the electrospinning process, the jet stability and morphology of polymer fibers obtained.[16] Previous research on electrospinning parameters affecting DP electrospun scaffolds were performed using the original classic DP[17], which has significantly smaller strain at break (61.33±11.37%) when compared to the new DP synthesized and explored here DP.[4] Moreover, the solvent used in previous research was pure chloroform, while here, a mixture of chloroform and hexafluoro-2-propanol in a ratio of 80:20 was used in order to allow easy dissolution of DP without involving subsequent heating step. Taking this into consideration, the fiber diameter of pure and emulsion electrospun DP fibers was compared using different wt % of DP (8, 10, 12 and 14) and different electrospinning parameters (voltage (10-17.5 kV) and flow rate (0.5-3 mL $h^{-1}$)). Similar trends were observed in single and emulsion electrospun DP fibers (FIG. 4A). For single electrospun DP fibers, decrease in average fiber diameter [µm] was observed with the increase in wt % of DP used, but without significant differences. A clear effect on fiber diameter upon differences in applied voltage [kV] was not visible. However, significant differences were obtained with differences in flow rates (mL $h^{-1}$) applied. Increasing the flow rate from 0.5 mL $h^{-1}$ to 3 mL $h^{-1}$ resulted in an average increase of fiber diameter from 3.83±2.12 m to 6.31±2.35 m. With increase in flow rate applied, a greater volume of solution is pumped out and while stretched with the same voltage, it leads to formation of thinner or thicker jets. However, too high flow rate may not allow for proper solvent evaporation before fiber deposition and increase in fiber defects or fiber fusion can be present.

For emulsion electrospun DP scaffolds, a significant increase in fiber diameter was observed with the increase of wt % of DP, from 8 to 14 wt % DP and increase in flow rate, from 0.5 mL $h^{-1}$ to 3 mL $h^{-1}$. Higher fiber diameters obtained with an increased wt % of DP can be correlated with increased in viscosity of the polymer solutions. As a result, low voltages (10 kV) with higher wt % (14 wt %) did not allow for proper fiber formation. The applied voltage only showed an effect in the range of 12.5, 15 and 17.5 kV (FIG. 4A). These findings are in agreement with earlier studies.[18]

Emulsion versus single electrospinning of DP had a major effect on the range of fiber diameters obtained. Emulsion electrospun DP scaffolds resulted in an average diameters from 1.79±0.17 μm up to 4.54±0.19 μm, while pure DP scaffolds ranged from 4.5±0.79 μm to 3.98±0.12 μm. Emulsion DP fibers produced with 8-12 wt % DP polymer solutions had significantly smaller fiber diameters when compared to pure electrospun DP scaffolds in the same range (FIG. 4B). This effect can be accounted for by the change in properties of the polymer solution (viscosity and surface tension) once the aqueous phase is introduced.[19] During emulsion electrospinning, the polymer jet undergoes increased and earlier splitting as well as increased instability, thus leading to decreased fiber diameters.

Figure 5:
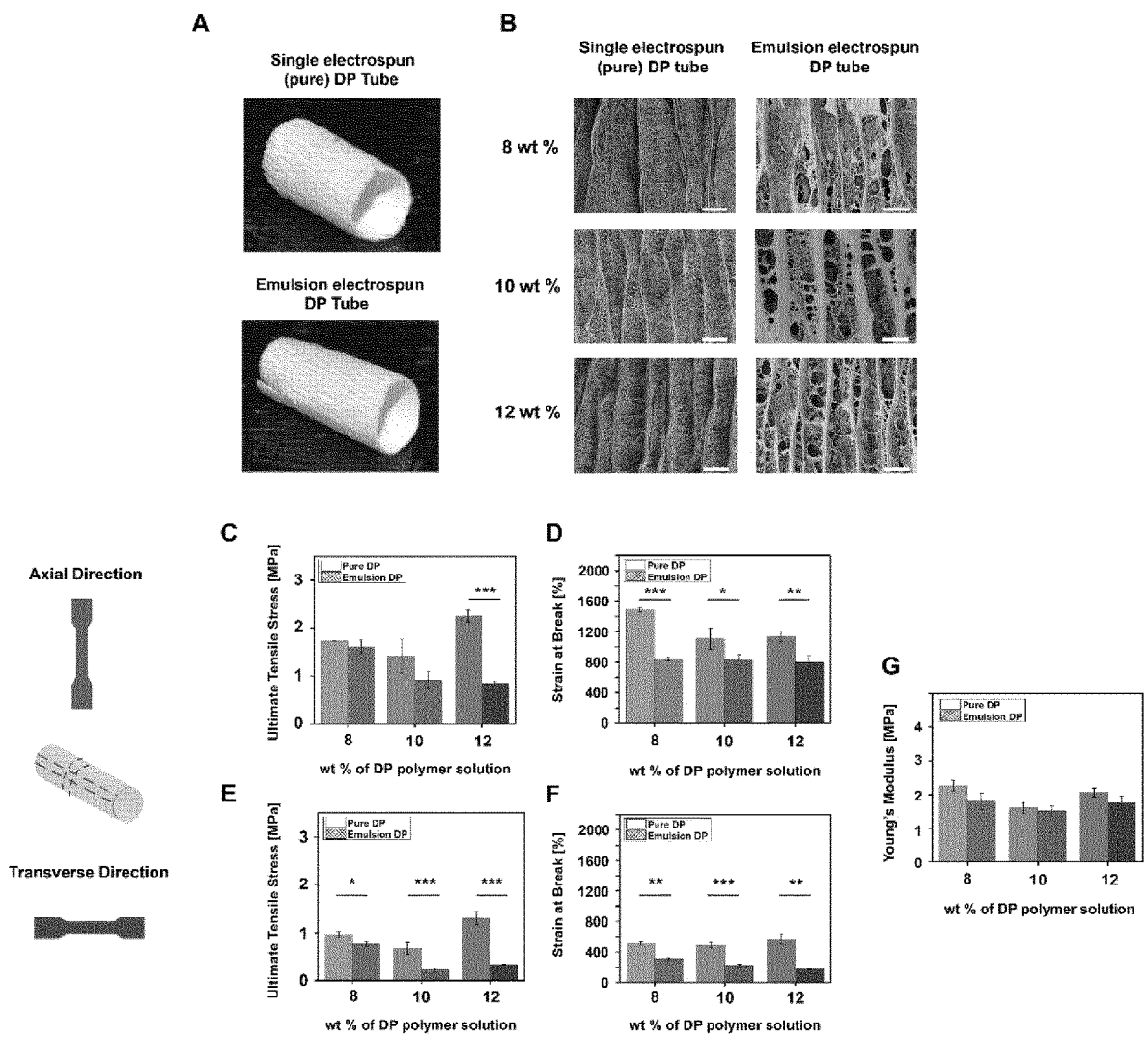
FIG. 5 Anisotropy in mechanical properties of single and emulsion electrospun DegraPol® tubes. A) Appearance of single (pure) and emulsion electrospun DP tubes. B) SEM micrographs of the top surface of single and emulsion electrospun DP tubes, showing "tertiary" structure formation by fiber fusion. C) Ultimate tensile stress (UTS) [MPa] and D) strain at break [%] of DP tubes measured in the axial direction. E) Ultimate tensile stress (UTS) [MPa] and F) strain at break [%] of DP tubes measured in the transverse direction. G) Young's modulus [MPa] of 8, 10 and 12 wt % DP scaffolds, single and emulsion electrospun. (*$p<0.05$, $p<0.01$, *$p<0.001$.) Scale bars: B) 150 μm.

Mechanical properties of emulsion electrospun DP scaffolds Variations of scaffold morphology and composition induce changes in the mechanical properties of the scaffolds and are highly dependent on the polymer.[20] The new DP explored here, with very high elasticity, allows for easy and surgeon-friendly handling, when it is pulled over the wound site. With the goal of adjusting for this desired property, mechanical testing of emulsion electrospun DP tubes (with incorporated FITC-BSA) was performed. To determine differences arising due to changes in electrospinning method, DP tubes were produced from different wt % of DP (8, 10 and 12) with single and emulsion electrospinning. Formation of tertiary structures by fiber fusion was observed in thick electrospun DP scaffolds (500-800 μm), resulting in fused fiber in the axial direction of the electrospun tubes (FIGS. 5A and B). This led to formation of parallel ridges along the rough surface of DP tubes in both methods. This effect was present only when DP was dissolved in chloroform and hexafluoro-2-propanol mixture and not in pure chloroform. Since this formation of ridges can influence the mechanical properties of the DP tubes, both directions of the tubes (axial and transverse) were tested. The major stretching of the DP tube during surgery handling happens in the transverse direction of the tube.

When compared to pure DP scaffolds, the ultimate tensile stress (UTS) [MPa] of emulsion electrospun DP scaffolds decreased in both tube directions (FIGS. 5C and E) and the UTS was lower in the transverse direction, compared to the axial direction. Emulsion electrospun scaffolds experienced significantly lower UTS in the transverse direction (0.759±0.055, 0.228±0.034, 0.338±0.013) when compared to pure DP scaffolds (0.962±0.055, 0.67±0.123, 1.295±0.132) for all wt % of DP. This difference can be due to scaffold's morphological differences, but also due to protein presence (in aqueous droplets) within the fibers, thus resulting in internal structural defects. Failure stresses of healthy rabbit Achilles tendons which are similar in strength as human flexor tendons have UTS in the range of 30 MPa.[6] The UTS of the electrospun DP scaffolds (1-2 MPa) are too low to act as reinforcement of the structural tendons which are not intended when applied in tendon repair in a clinical setting. Significant decrease in strain at break [%] from pure DP to emulsion electrospun DP was observed for both directions of the tube (FIGS. 5D and F). Moreover, significant decrease in strain at break [%] in the transverse direction when compared to the axial direction for all samples was observed. In the transverse direction, emulsion electrospun scaffolds had strain at break of 311.36±16.8, 224.16±18.9 and 175.48±6.4%, for 8, 10 and 12 wt % DP, respectively. Pure DP scaffolds had higher values, i.e. 843.9±22.75, 827.5±65.96 and 795±91.61, for 8, 10 and 12 wt % DP respectively (FIG. 5F). However, the more fragile emulsion electrospun DP scaffolds could still be stretched in the transverse direction on average 2 times from their initial size before breaking. This decrease in the strain at break is present due to the "tertiary structure" obtained by fiber fusion (FIG. 5B) when scaffolds started becoming thicker. Thicker scaffolds had ridges formed by fibers fused that could act as scaffold defects and decrease the scaffold's mechanical properties. These fused fiber bundles created along the axial direction of the tube, run along in the same direction as tendon collagen fibers, but perpendicular to the direction of tube stretching, thereby resulting in a decreased strain at break in the transverse direction. However, the properties of the emulsion electrospun scaffolds still allow successful handling and application during surgery.

Young's modulus [MPa] of emulsion electrospun scaffolds (1.8±0.24, 1.50±0.15 and 1.75±0.21) when compared to single spun scaffolds (2.26±0.15, 1.60±0.17 and 2.06±0.13) for each wt % of DP decreased slightly, but not significantly (FIG. 5G). As Young's moduli of healthy rabbit tendons are in the range of 100 MPa[21], the comparatively low moduli of both emulsion and pure DP scaffolds are far from being similar to the tendons, but this is not relevant when scaffolds are used as drug delivery devices.

Release Kinetics of Fluorescein and FITC-BSA from DP Scaffolds

To study the release kinetics of entrapped molecules from emulsion electrospun DP scaffolds, fluorescein and FITC-BSA were incorporated as model biomolecules with low (376.27 g mol$^{-1}$) and high (66 kDa) molecular weights, respectively. The scaffolds were thereby spun with different wt % of DP, as well as, two different flow rates (1 and 3 mL h$^{-1}$) to tune the fiber diameters while maintaining the same applied voltage (12.5-13 kV). As revealed by confocal laser scanning microscopy, the molecules were randomly dispersed within the fibers (FIG. 6A) similar to other polymers [21] and no core-shell fibers[22] were formed.

Figure 6:
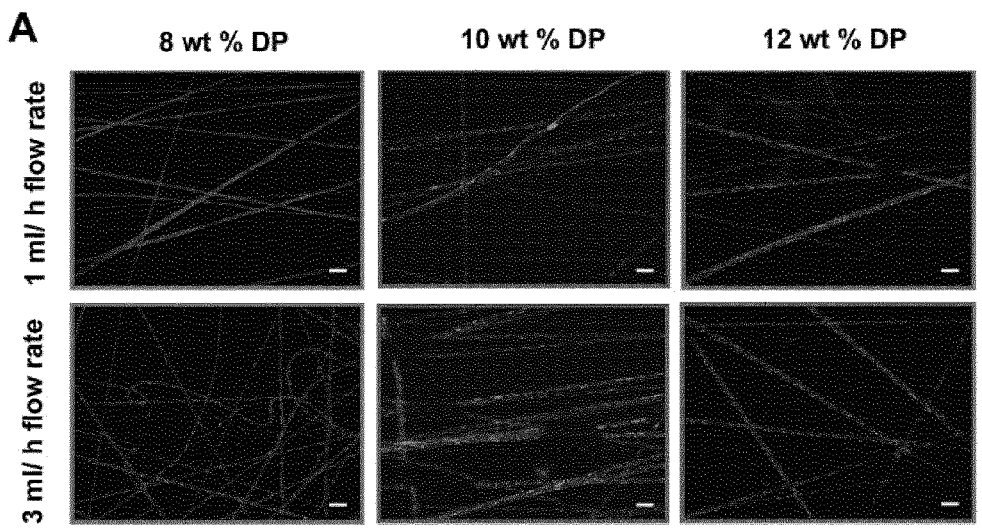
FIG. 6 Characterization of DegraPol® emulsion electrospun scaffolds as a delivery system using two model molecules. A) CLSM images of emulsion electrospun DegraPol® fibers with incorporated FITC-BSA at different flow rates (ml h$^{-1}$) and wt % of DegraPol® in the polymer solution. B) In vitro cumulative release [%] of fluorescein from DegraPol scaffolds as a function of flow rate used (1 ml h$^{-1}$ and 3 ml h$^{-1}$, 10 wt % DP). C) In vitro cumulative release [%] of fluorescein from DegraPol scaffolds as a function wt % of DP polymer solution used, at a constant flow rate (1 ml h$^{-1}$). D) In vitro cumulative release [%] of FITC-BSA from DegraPol scaffolds as a function of flow rate used (1 ml h$^{-1}$ and 3 ml h$^{-1}$, 10 wt % DP). E) In vitro cumulative release [%] of fluorescein from DegraPol scaffolds as a function wt % of DP polymer solution used, at a constant flow rate (1 ml h$^{1}$). Scale bars: A) 10 μm.
Figure 6:
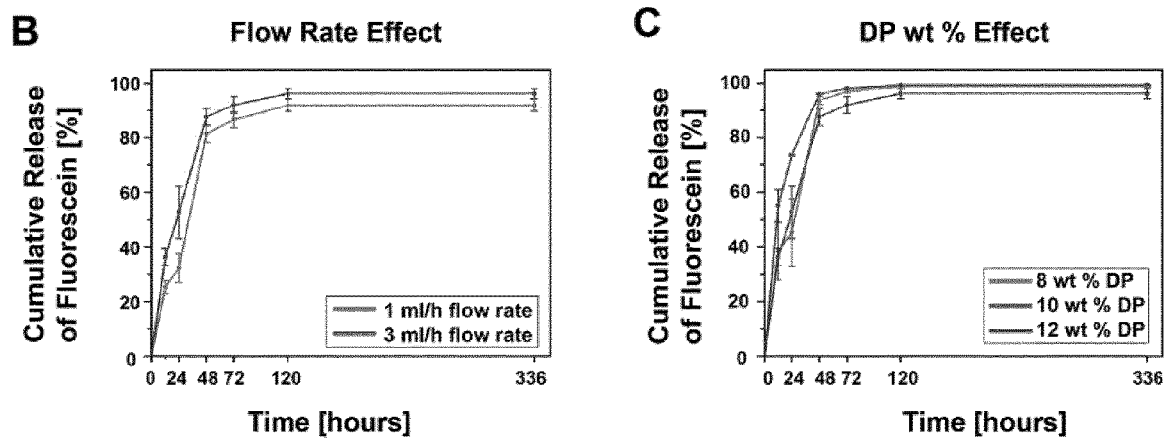
Figure 6:
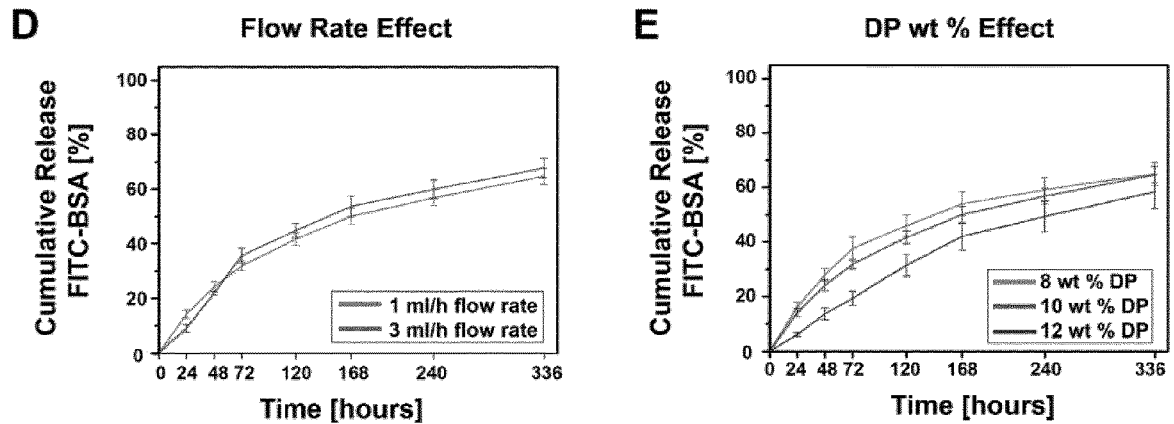

The cumulative release of incorporated fluorescein reached already 95% after 48 hours without further changes up to 5 days (FIGS. 6B and C), suggesting a burst-mediated release independent of the mentioned adjustable parameters. On the other hand, the release profile of FITC-BSA from DP scaffolds was a more sustained one. In 24 hours, less than 20% of FITC-BSA were released from the fibers, with a gradual increase every next time point. The maximum release within 14 days ranged from 58.42±6.18% for 12 wt % DP up to 64.90±4.26% for 8 wt % DP (FIG. 6E). No significant differences are visible in the FITC-BSA release profile from fibers with different wt % of DP (FIG. 6E) or if produced with different flow rates (ml h$^{-1}$) (FIG. 6D).

As a polymer powder, DP is biodegradable within 3 months, mainly by hydrolytic degradation. Degradation of the scaffolds in aqueous conditions over the time period of 14-30 days was not visible (data not shown). Taking this into account, the release of molecules from the electrospun fibers in the studied aqueous environments (PBS buffer) is expected to happen primarily due to diffusion mechanism and not due to the degradation of the fibers within the time frame studied here (up to 14 days). This significantly can differ in in vivo setting, where at a wound site, the presence of different macrophages or MMPs can accelerate the polymer degradation.[24]

The differences in the release of fluorescein and FITC-BSA are due to their differences in molecular weight and size too.[25] Fluorescein is readily dissolvable in water and upon placing the scaffolds in aqueous environment it can readily dissolve in it, without being adsorbed on the surface of the scaffolds. In contrast, BSA as a protein easily adsorbs on surfaces. It has stronger interactions with hydrophilic surfaces and can cover up to 95% of the surface. On hydrophobic surfaces it usually covers around 50% of the surface.[26] DP being hydrophobic, released BSA can adsorb up to some extent on the surface and be in an equilibrium of protein release and protein re-adsorption on the scaffold surface.

In addition, the DP fibers are experiencing quite smooth surfaces without visible nanopores on their fiber surface. Fluorescein having a Stokes radius of 0.55 nm can easily diffuse out of the DP fibers. On the other hand, larger proteins like BSA (Stokes radius=3.48 nm) might experience limited diffusion through the fibers, with major part of released BSA being close to or on the fiber surface, and the rest that is inside the fibers to be released only after scaffold degradation.

Release Kinetics of PDGF-BB from DP Scaffolds

To assess the possible interaction of PDGF-BB (24.3 kDa disulfide-linked homodimer of two P chains) with DP surfaces that might play a role in its release from the scaffolds, PDGF-BB was physically adsorbed on pure DP scaffolds and immunostaining was performed in order to detect it on the surface of the fibers. From the image (FIG. 7A) it is visible that its distribution on the surface of DP fibers was uniform. On the other hand, emulsion electrospun DP scaffolds were also immunostained for PDGF-BB and sparse, randomly distributed PDGF-BB was visualized, that got on the surface of the scaffolds during the production procedure, with the rest incorporated within the polymer fibers and not accessible for detection (FIG. 7B).

Figure 7:
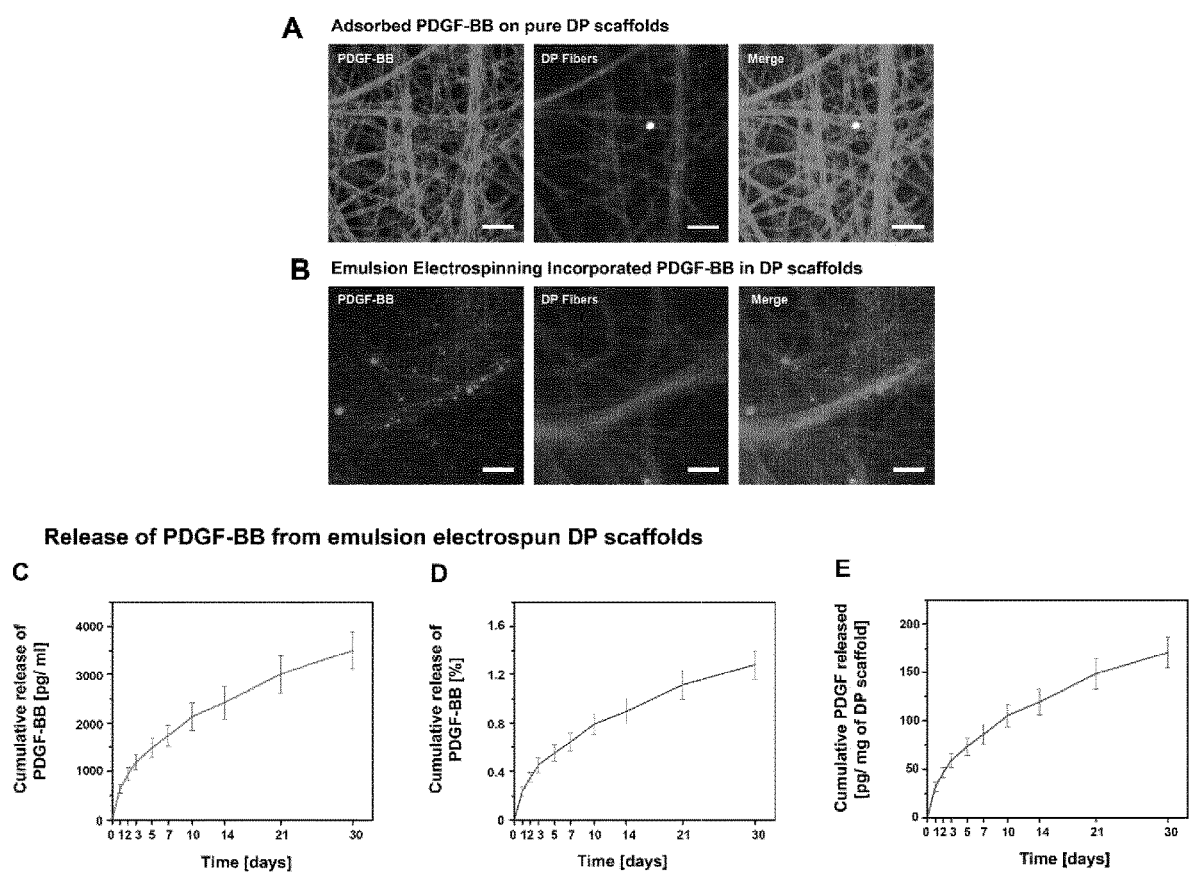
FIG. 7 PDGF incorporation within DegraPol® scaffolds and its release profile from emulsion electrospun DegraPol® scaffolds. A) CLSM images of physically adsorbed PDGF-BB on pure DP scaffolds detected by immunostaining methods. B) Emulsion electrospun DP scaffolds with incorporated PDGF-BB. C) In vitro cumulative release of PDGF-BB [pg ml$^{-1}$]. D) In vitro cumulative release of PDGF-BB [%] calculated from theoretical loading. E) pg of PDGF-BB released per mg of DP scaffold in in vitro conditions. Electrospinning parameters: C), D) and E) 1 ml h$^{-1}$, 11-12.5 kV, 12 wt % DP. Scale bars: A) and B) 20 μm.

From all electrospinning parameters screened and release kinetics of model molecules studied, 12 wt % DP, 11-12 kV applied voltage, 1 ml mL$^{-1}$ flow rate and 20 cm working distance were chosen as best parameters for the production of the bioactive emulsion electrospun DP scaffolds. The in vitro PDGF-BB release from emulsion electrospun DP fibers showed similar trend to FITC-BSA, i.e. a more sustained release, rather than burst release as fluorescein exhibited (FIG. 7). Within 30 days, the cumulative release of PDGF-BB in pg ml$^{-1}$ reached around 3500 µg ml$^{-1}$, i.e. 3.5 ng ml$^{-1}$ (FIG. 7C). Due to the sensitivity of growth factors, the DP scaffolds were not dissolved in chloroform and PDGF-BB was not extracted at the end of the release period. To obtain quantitative data on the release, the cumulative percentage of PDGF-BB released was calculated using a theoretical loading (13.33 ng/mg of DP scaffold). This resulted in a very low cumulative release of PDGF [%] of average 1.3% within 30 days (FIG. 7D). Emulsion electrospinning does not offer 100% loading efficiency, thus we hypothesize that this cumulative release % is larger. In addition, the amount of PDGF-BB released was normalized to the weight of DP scaffold, resulting with an initial release of 31.81±1.71 µg mg$^{-1}$ of DP and within 30 days having a cumulative release of 170.63±5.71 µg mg$^{-1}$ of DP (FIG. 7E). PDGF-BB physiological concentrations in whole blood have been determined to be in the range of 3.3±0.9 ng mL$^{-1}$ and increase to 17±8 ng mL$^{-1}$ in platelet-rich plasma (PRP)[27]. PRP has been suggested as a strategy for promoting wound-healing cascade.[28] In in vitro conditions, within 30 days period the released PDGF-BB amounts from the scaffolds were within the physiological range of whole blood. Due to different conditions and enzymatic DP degradation possible in in vivo settings, one should expect different release of PDGF-BB, with possibly larger amount of PDGF-BB released, within 2-4 weeks.

PDGF-BB Effect on Rabbit Tenocyte Proliferation and Bioactivity Assays

Figure 8:
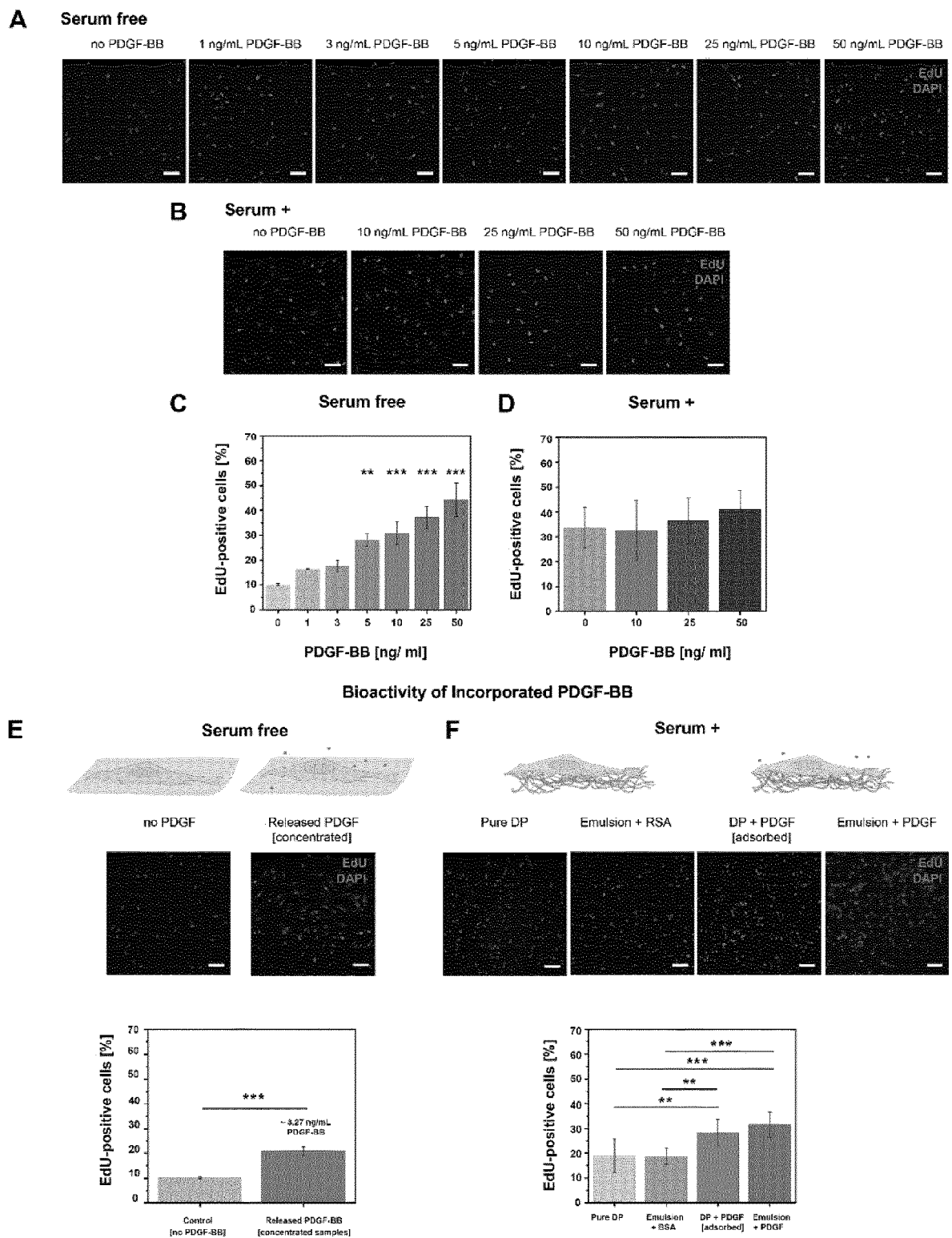
FIG. 8 Effect of PDGF-BB on rabbit tenocytes and bioactivity of incorporated and released PDGF-BB.

To determine the concentration at which PDGF-BB has a significant effect on rabbit tenocyte proliferation, different concentrations of PDGF-BB were screened in serum free and serum$^+$ medium. Serum starved synchronized cells were exposed to 1-50 ng/ml PDGF-BB for 24 hours. As quantitative measure of proliferating cells, the percentage of EdU-positive cells (marking DNA synthesis in proliferating cells) was determined for each condition. In serum free medium, the lowest PDGF-BB concentrations (1 and 3 ng mL$^{-1}$) already induced an increase in cell proliferation when compared to a control, but the increase in cell proliferation being significant only at 5 ng mL$^{-1}$ and higher PDGF-BB concentrations (FIGS. 8A and C). These results are in agreement with the effect of PDGF-BB on proliferation of avian tendon fibroblasts.[29] In the presence of serum, the tenocytes showed high proliferation rate already at day 1 and a slight, but not significant increase in proliferation with increase in PDGF-BB concentrations (10-50 ng mL$^{-1}$) (FIGS. 8B and D). Taking this into account, bioactivity of concentrated samples of released PDGF-BB was assessed in serum free conditions, where its amount was in the lower concentration ranges tested (FIG. 8E). Released PDGF-BB overtime from the electrospun scaffolds lead to increase in tenocyte proliferation when compared to no PDGF-BB presence, thus confirming that PDGF-BB retains bioactivity after electrospinning and release (FIG. 8E). In addition, WST-1 proliferation assay was performed with rabbit tenocytes cultured in serum free and serum$^+$ conditions to observe their metabolic activity (proliferation) and viability within 14 days, without or with PDGF-BB (5, 10, 25 and 50 ng mL$^{-1}$). Tenocytes cultured in serum free conditions did not show increased mitochondrial metabolic activity and were viable, but their metabolic activity and proliferation increased significantly with the addition of PDGF-BB (Figure S2A). Tenocytes cultured in serum$^+$ medium, showed higher proliferation rates than tenocytes in serum free conditions, however the proliferative effect of PDGF-BB after 14 days, was mostly visible and significant at 25 and 50 ng mL$^{-1}$ PDGF-BB concentrations (Figure S2B).

To obtain a more physiologically relevant bioactivity assay in serum$^+$ conditions, tenocyte proliferation was tested directly on pure and bioactive DP scaffolds, expecting that local PDGF-BB concentration is higher due to the equilibrium of growth factor bound to the scaffold surface and released into the medium. Tenocytes seeded on electrospun scaffolds (in serum$^+$ conditions) generally had decreased proliferation, ~18% (FIG. 8F) when compared to seeded tenocytes on glass coverslips (Figure S3B). These differences can be correlated with recently published study where has been shown that cell mediated fiber recruitment drives extracellular matrix mechanosensing and regulates cellular functions in fibrillary microenvironments. Lower fiber/network stiffness enabled cells to recruit nearby fibers leading to increased local adhesive ligand density, cell spreading and proliferating signaling.[30] We hypothesize that through this mechanism, tenocytes seeded on DP electrospun scaffolds, sensed quite dense fiber networks, resulting in a decrease in proliferation when compared to cell seeded on coverslips.

Bioactive emulsion electrospun DP scaffolds showed a significant increase in proliferation (31.57±5.09%), when compared to pure DP scaffolds without PDGF-BB (18.96±6.82%) or empty emulsion electrospun DP with only BSA incorporated as a control (18.70±3.34%). Pure DP scaffolds with physically adsorbed PDGF-BB on the surface were used as a positive control. Tenocytes seeded onto these scaffolds experienced significant increase in proliferation (28.37±5.21) when compared to the pure DP scaffolds or empty emulsion electrospun DP scaffolds (FIG. 8F). Tenocytes seeded on scaffolds incorporating PDGF-BB in any of the two ways, had increased proliferation without significant differences between physically adsorbed or emulsion incorporated PDGF-BB. This data suggests indeed higher local concentration of PDGF-BB on the scaffold surface sensed by the cells seeded onto the bioactive emulsion electrospun scaffolds, with some amount of it eventually being released into the medium. It also suggests that the incorporated PDGF-BB into the scaffolds is still biologically active and leads to increase in cellular proliferation.

Exposure of NIH3T3 cells to low concentrations of PDGF-BB ($<2$ ng mL$^{-1}$) was shown to have greater effect on cell migration rather than cell proliferation, due to differences in endocytotic routes of the PDGF receptor after PDGF binding. Higher PDGF-BB concentrations (~30 ng mL$^{-1}$) resulted in increased cell proliferation.[13] Similar behavior can be seen in the rabbit tenocyte proliferation, where 1 and 3 ng mL$^{-1}$ did not lead to significant increase in cell proliferation, but >5 ng mL$^{-1}$ PDGF-BB did. Since bioactive DP tubes are to be directly and locally applied at the wound site, with cells binding to the scaffold directly, we expect to have a condition closely resembling the serum$^+$ condition of bioactivity assay, where some tenocytes would be exposed to higher local PDGF-BB concentration and some experience the migratory effect of PDGF-BB administration.

CONCLUSION

Out data suggest that emulsion electrospun DP tubes are promising for Achilles tendon rupture repair and we identified conditions under which they can be produced to be sufficiently elastic and bioactive. We have screened and defined a range of electrospinning parameters best suited for emulsion electrospinning of DP, incorporating different biomolecules within the polymer fibers. Emulsion electrospinning of DP lead to fiber diameter decrease and decrease in the strain of break [%] in both tube's directions, compared to pure DP, but still offering enough scaffold elasticity for successful clinical use. High molecular weight FITC-BSA and PDGF-BB experienced a sustained release kinetics from the emulsion electrospun DP scaffolds, compared to a burst release of low molecular weight fluorescein form the same. However, large fraction of bioactive molecules was left inside the DP fibers and was not released under the tested in vitro conditions. The released PDGF-BB was shown to be bioactive, leading to increased proliferation of rabbit tenocytes in in vitro under serum free conditions. In addition, tenocytes seeded directly onto bioactive DP scaffolds showed increased proliferation in serum$^+$ conditions, suggesting higher local PDGF-BB concentration on the scaffolds surface. As a next step, the bioactive DP tube, delivering PDGF-BB is aimed to be implanted and tested in in vivo rabbit model.

REFERENCES

[1] S. Thomopoulos, W. C. Parks, D. B. Rifkin, K. A. Derwin, *J. Orthop. Res.* 2015, 33, 832.

[2] D. Elliot, T. Giesen, *Hand clin.* 2013, 29, 191.

[3] J. C. Goh, H. W. Ouyang, S. H. Teoh, C. K. Chan, E. H. Lee, *Tissue Eng.* 2003, 9, S31.

[4] a) J. Buschmann, M. Calcagni, G. M. Burgisser, E. Bonavoglia, P. Neuenschwander, V. Milleret, P. Giovanoli, *J. Tissue Eng. Regen. Med.* 2015, 9, 584; b) J. Buschmann, G. MeierBurgisser, E. Bonavoglia, P. Neuenschwander, V. Milleret, P. Giovanoli, M. Calcagni, *J. Tissue Eng. Regen. Med.* 2013, 7, 413.

[5] a) V. Milleret, M. Simonet, A. G. Bittermann, P. Neuenschwander, H. Hall, *J. Biomed. Mat. Res. B Applied Biomater.* 2009, 91, 109; V. Milleret, B. Simona, P. Neuenschwander, H. Hall, *Eur. Cell Mater.* 2011, 21, 286; c) S. A. Riboldi, M. Sampaolesi, P. Neuenschwander, G. Cossu, S. Mantero, *Biomaterials.* 2005, 26, 4606.

[6] a) J. Buschmann, G. Puippe, G. M. Bürgisser, E. Bonavoglia, P. Giovanoli, M. Calcagni, *Connect. Tissue Res.* 2014, 55, 123; b) G. M. Bürgisser M. Calcagni, Müller A, E. Bonavoglia, G Fessel, J. G. Snedeker, P. Giovanoli, J. Buschmann, *Biomed. Res. Int.* 2014, 2014, 656240.

[7] a) Y. Qian, Z. Zhang, L. Zheng, R. Song, Y. Zhao. *J. Nanomat.* 2014, 2014, 964621. b) V. Milleret, B. Simona, P. Neuenschwander, H. Hall, *Eur. Cell Mater.* 2011, 21, 286.

[8] a) N. Bachl, W. Derman, L. Engebretsen, G. Goldspink, M. Kinzlbauer, H. Tschan, P. Volpi, D. Venter, B. Wessner, *J. Sports Med. Phys. Fitness.* 2009, 49, 346; b) L. V. Gulotta, S. A. Rodeo, *Clin. Sports Med.* 2009, 28, 13; c) M. A. Sandrey, *J. Athl. Train.* 2014, 49, 428.

[9] a) S. Thomopoulos, M. Zaegel, R. Das, F. L. Harwood, M. J. Silva, D. Amiel, S. Sakiyama-Elbert, R. H. Gelberman, *J. Orthop. Res.* 2007, 25, 1358; b) S. Thomopoulos, R. Das, M. J. Silva, S. Sakiyama-Elbert, F. L. Harwood, E. Zampiakis, H. M. Kim, D. Amiel, R. H. Gelberman, *J. Orthop. Res.* 2009, 27, 1209; c) Uggen, J. Dines, M. McGarry, D. Grande, T. Lee, O. Limpisvasti, *Arthroscopy.* 2010, 26, 1456.

[10] a) T. Briggs, T. L. Arinzeh, *J. Biomed. Mat. Res. A.* 2014, 102, 674; b) X. Hu, S. Liu, G. Zhou, Y. Huang, Z. Xie, X. Jing, *J. Control Release.* 2014, 185, 12. c) H. Jiang, L. Wang, K. Zhu, *J. Control Release.* 2014, 193, 296. d) W. Ji, Y. Sun, F. Yang, J. J. J. P. van den Beucken, M. Fan, Z. Chen, J. A. Jansen, *Pharm. Res.* 2011, 28, 1259.

[11] A. J. Meinel, O. Germershaus, T. Luhmann, H. P. Merkle, L. Meinel, *Eur. J. Pharm. Biopharm.* 2012, 81, 1.

[12] a) T. Briggs, T. L. Arinzeh, *J. Biomed. Mat. Res. A,* 2014, 102, 674; b) I. C. Liao, S. Y. Chew, K. W. Leong, *Nanomedicine (Lond.).* 2006, 1, 465; c) Y. Liao, L. Zhang, Y. Gao, Z. T. Zhu, H. Fong, *Polymer (Guildf).* 2008, 49, 5294; d) X. Xu, X. Zhuang, X. Chen, X. Wang, L. Yang, X. Jing, *Macromol. Rapid Commun.* 2006, 27, 1637; e) Qi, P. Hu, J. Xu, A. Wang, *Biomacromolecules* 2006, 7, 2327; f) X. Li, Y. Su, S. Liu, L. Tan, X. Mo, S. Ramakrishna, *Colloids Surf B. Biointerfaces.* 2010, 75, 418.

[13] A. De Donatis, G. Comito, F. Buricchi, M. C. Vinci, A. Parenti, A. Caselli, G. Camici, G. Manao, G. Ramponi, P. Cirri, *J. Biol. Chem.* 2008, 283, 19948.

[14] R. Pal, *AIChE Journal.* 1996, 42, 3181.

[15] a) L. Larrondo, R. St. John Manley, *J. Polym. Sc. Polym. Phys. Ed.* 1981, 19, 909; b) S. Sukigara, M. Gandhi, J. Ayutsede, M. Micklus, F. Ko, *Polymer.* 2003, 44, 5721; c) P. Gupta, C. Elkins, T. E. Long, G. L. Wilkes, *Polymer.* 2005, 46, 4799.

[16] a) V. Beachley, X. Wen, *Mater. Sci. Eng. C Mater. Biol. Appl.* 2009, 29, 663; b) S. V. Fridrikh, J. H. Yu, M. P. Brenner, G. C. Rutledge, *Phys. Rev. Lett.* 2003, 90, 144502; V. Jacobs, R. D. Anandjiwala, M. Maaza, *J. Appl. Polym. Sci.* 2010, 115, 3130.

[17] Milleret, B. Simona, P. Neuenschwander, H. Hall, *Eur. Cell Mater.* 2011, 21, 286;

[18] a) S. Kidoaki, I. K. Kwon, T. Matsuda, *J. Biomed. Mater. Res.* B Appl. Biomater. 2006, 76, 219; b) V. Pillay, C. Dott, Y. E. Choonara, C. Tyagi, L. Tomar, P. Kumar, L. C. du Toit, V. M. K. Ndesendo, *J. Nanomat.* 2013, 2013, 789289.

[19] J. C. Sy, A. S. Klemm, V. P. Shastri, *Adv. Mater.* 2009, 21, 1814.

[20] a) S. G. Kumbar, R. James, S. P. Nukavarapu, C. T. Laurencin, *Biomed. Mater.* 2008, 3, 034002; b) D. M. Lavin, L. Zhang, S. Furtado, R. A. Hopkins, E. Mathiowitz, *Acta Biomater.* 2013, 9, 4569.

[21] H. J. Goodman, J. Choueka, *Hand Clin.* 2005, 21, 129.

[22] S. Y. Chew, J. Wen, E. K. F. Yim, K. W. Leong, *Biomacromolecules.* 2005, 6, 2017.

[23] Y. Yang, X. Li, M. Qi, S. Zhou, J. Weng, *Eur. J. Pharm. Biopharm.* 2008, 69, 106.

[24] a) J. M. Anderson, A. Rodriguez, D. T. Chang, *Semin. Immunol.* 2008, 20, 86; b) E. M. Christenson, M. Dadsetan, M. Wiggins, J. M. Anderson, A. Hiltner, *J. Biomed. Mat. Res.* A. 2004, 69, 407; c) R. S. Labow, D. Sa, L. A. Matheson, D. L. Dinnes, J. P. Santerre, *Biomaterials.* 2005, 26, 7357; d) R. S. Labow, E. Meek, L. A. Matheson, J. P. Santerre, *Biomaterials.* 2002, 23, 3969.

[25] D. M. Lavin, L. Zhang, S. Furtado, R. A. Hopkins, E. Mathiowitz, *Acta Biomater.* 2013, 9, 4569.

[26] Y. L. Jeyachandran, E. Mielczarski, B. Rai, J. A. Mielczarski, *Langmuir.* 2009, 25, 11614.

[27] B. L. Eppley, J. E. Woodell, J. Higgins, *Plast. Reconstr. Surg.* 2004, 114, 1502.

[28] D. Docheva, S. A. Miiller, M. Majewski, C. H. Evans, *Adv. Drug Deliv. Rev.* 2015, 84, 222.

[29] A. J. Banes, M. Tsuzaki, P. Hu, B. Brigman, T. Brown, L. Almekinders, W. T. Lawrence, T. Fischer, *J. Biomech.* 1995, 28, 1505.

[30] B. M. Baker, B. Trappmann, W. Y. Wang, M. S. Sakar, I. L. Kim, V. B. Shenoy, J. A. Burdick, C. S. Chen, *Nat. Materials.* 2015, 14, 1262.

Example 2

Application of PDGF-BB Loaded DegraPol Tubes in Rabbit Achilles Tendons

Three weeks post-surgery, double-layered DegraPol® tubes having PDGF-BB incorporated by emulsion electrospinning and implanted around a fully transsected rabbit Achilles tendon being repaired with a conventional 4-strand Becker suture led to a higher ultimate failure load of extracted tendons compared to DegraPol® tubes fabricated in the same way, however, without incorporation of PDGF-BB (FIG. 9a) (t test to compare failure load of the two groups (±PDGF-BB): p=0.083). The same was observed for ultimate stress (FIG. 9b) (t test to compare the ultimate stress of the two groups (±PDGF-BB): p=0.026). The addition of this growth factor showed therefore to beneficially enhance tendon healing. As such, most occurring problems after tendon rupture and repair can be addressed; adhesion formation is reduced by the tube acting as a physical barrier and tendon strength is enhanced by incorporation of this growth factor-lowering the risk of re-rupture[1].

[1] Elliot, D. & Giesen, T. Primary Flexor Tendon Surgery: The Search for a Perfect Result. Hand Clin. 29, 191-206, doi:10.1016/j.hcl.2013.03.001 (2013).

Example 3

Application of Different DegraPol Tubes in Rabbit Achilles Tendons

FIG. 10 shows a comparison of various biomechanical parameters determined three weeks post-surgery of fully transsected rabbit Achilles tendons being repaired with a conventional 4-strand Becker suture. One series of experiments represented with black bars in the figure was made using emulsion electrospun DegraPol tubes, whereas another series of experiments represented with grey bars was made with coaxially electrospun tubes. In each of these two series, a comparison was made between three groups, namely, a group receiving the application of a tube made with DegraPol® only (denoted by "DegraPol Tube"), a group receiving the application of a tube made with DegraPol® incorporating the growth factor PDGF-BB (denoted by "DegraPol Tube+PDGF-BB") and a group receiving no tube (denoted by "Control"). The measured properties were: (a) tendon length in mm, (b) cross sectional area (CSA) in $cm^2$, (c) load until failure in N, (d) failure stress in MPa, (e) stiffness in N/mm, and (f) elastic modulus in MPa.

Figure 10A:
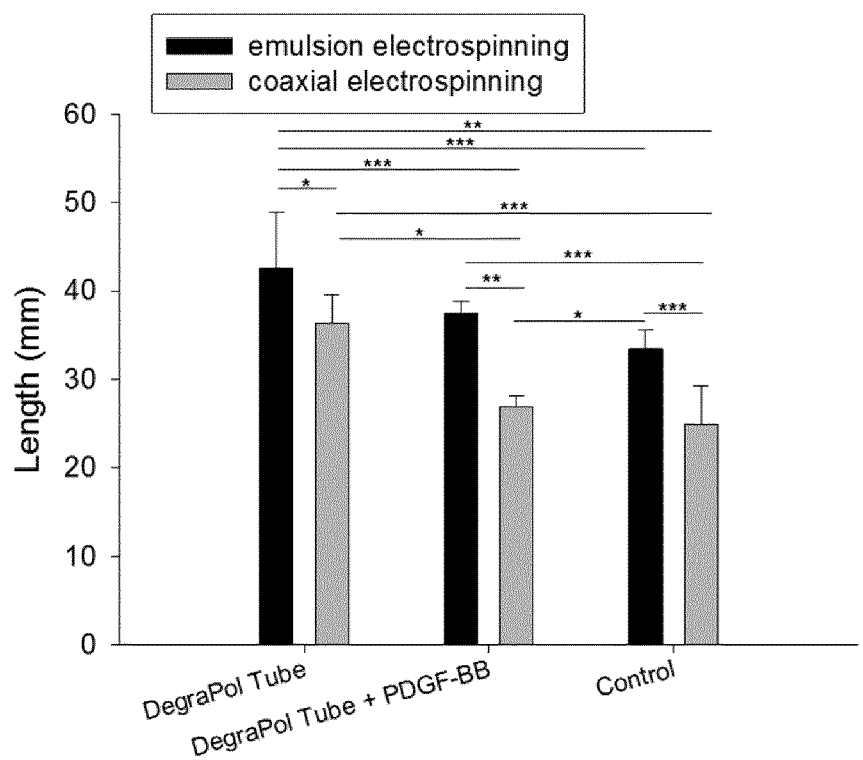
Figure 10B:
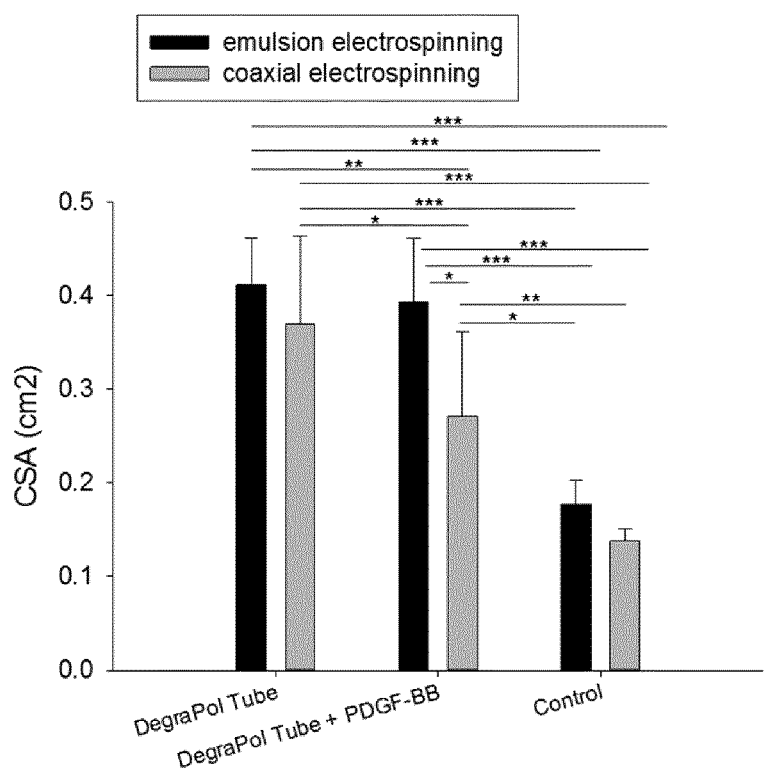
Figure 10C:
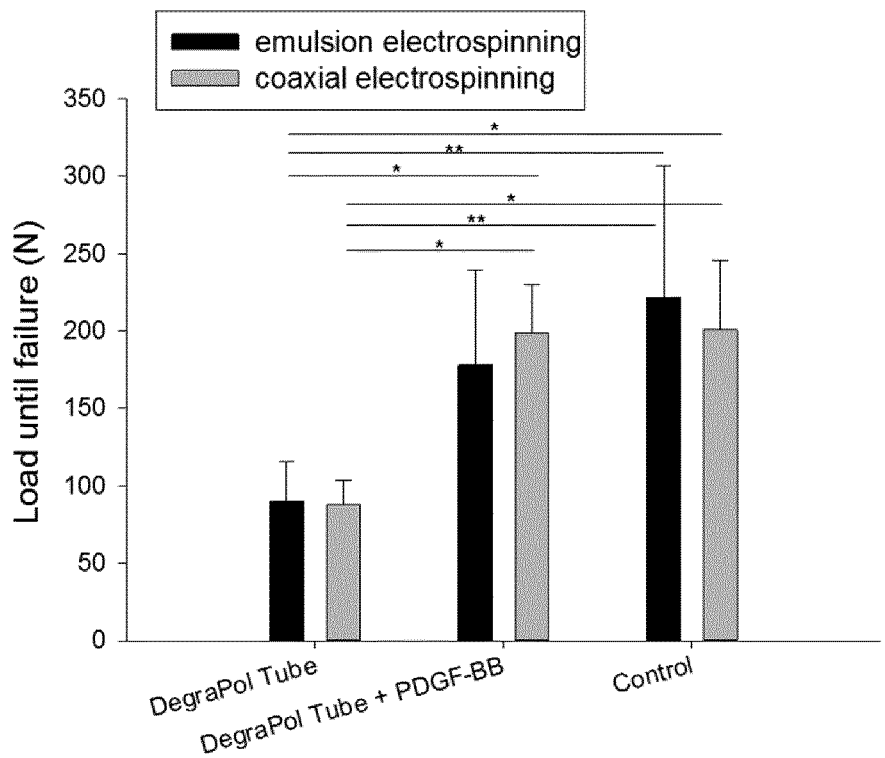
Figure 10D:
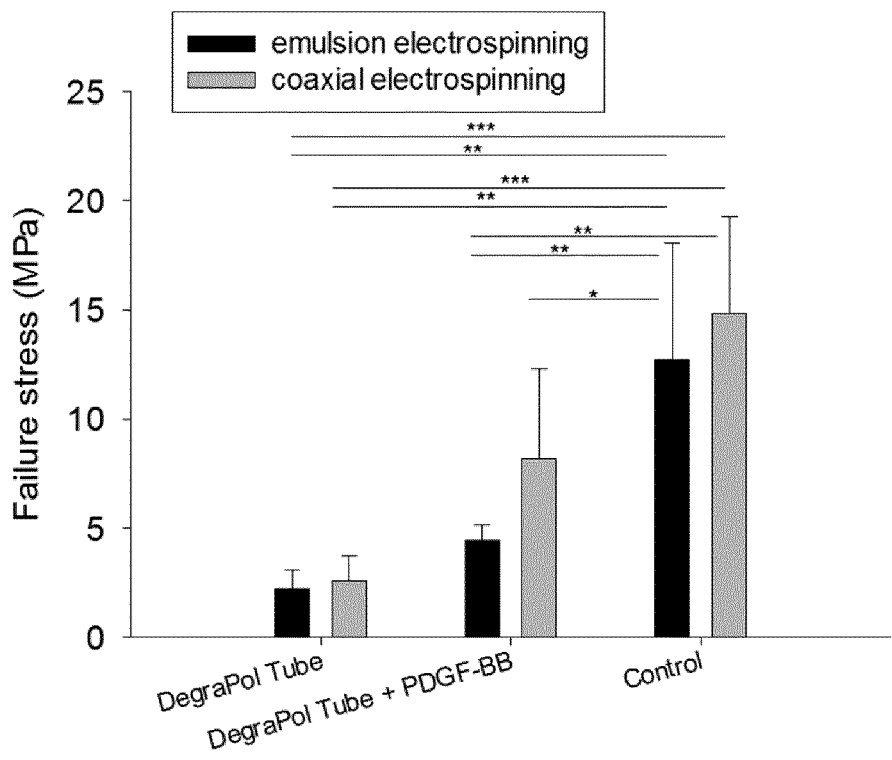
Figure 10E:
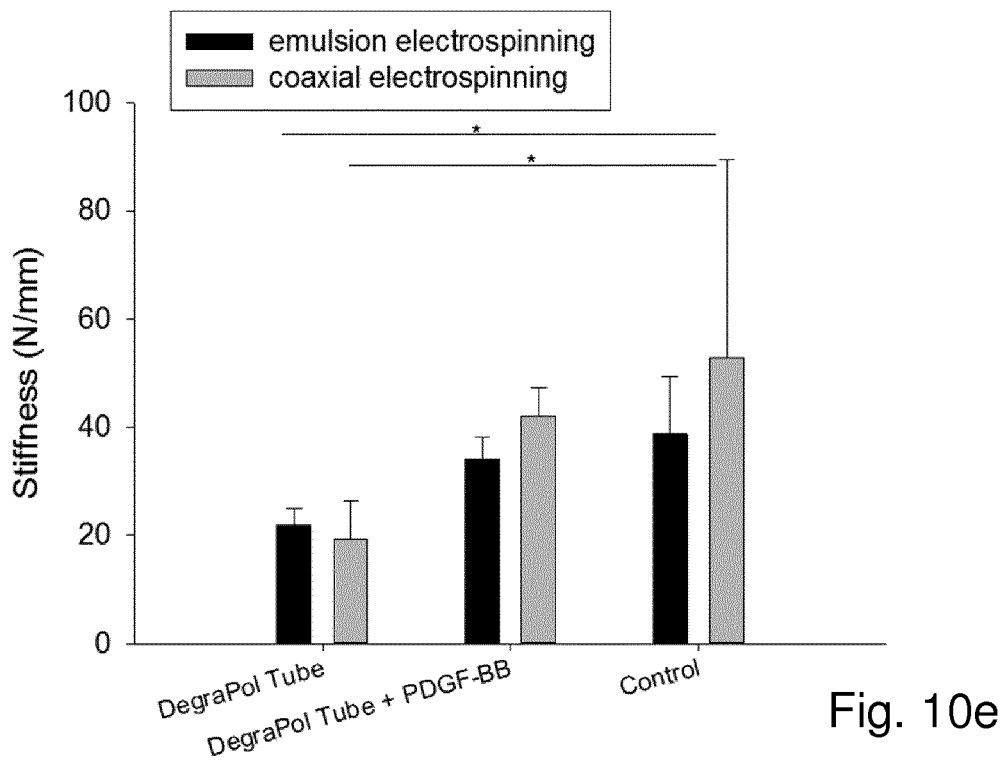
Figure 10F:
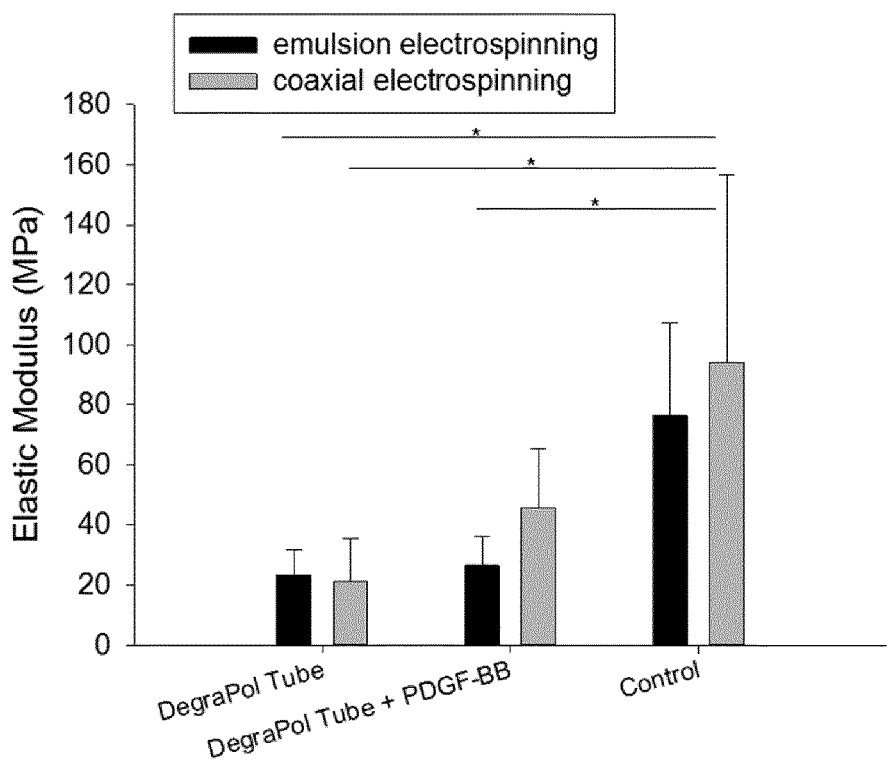

According to a one-way analysis of variance (one-way ANOVA) performed to test the differences between groups in all the experiments, the load until failure achieved after tendon repair using coaxially electrospun tubes containing PDGF-BB was significantly larger than in the case of unfilled coaxially electrospun tubes (see FIG. 10c). If using a simple t-test, a significant difference also holds for a corresponding comparison regarding stiffness (see FIG. 10e).

The invention claimed is:

1. A device for repair surgery of cylindrical organs comprising a tubular sheath (T) made of a mesh of elastic fibers formed by electrospinning at least one biocompatible and biodegradable polymer,
    said tubular sheath having a Young elasticity modulus of about 0.1 to about 4 MPa and a strain at break of about 50 to about 1,000%, said tubular sheath having a first wall surface and a second wall surface substantially parallel thereto, said first wall surface being smooth ($W_S$) and said second wall surface being rough ($W_R$), wherein
    said elastic fibers comprise
        first fibers consisting of a first one of said polymers in neat form, and second fibers consisting of a second one of said polymers with an admixture of a therapeutic agent adapted to stimulate regrowth processes of a predetermined cylindrical organ, said tubular sheath comprising a first tubular region adjacent to said first wall and a second tubular region adjacent to said second wall, said first tubular region being formed of said first fibers and said second tubular region being formed of said second fibers.

2. The device according to claim 1, wherein said first polymer and said second polymer are the same polymer.

3. The device according to claim 1, wherein at least said second polymer is a biodegradable polyester urethane block copolymer with poly-hydroxy-butyrate as a hard segment and ε-caprolactone as a soft segment.

4. The device according to claim 3, wherein said soft segment has an average molecular weight of about 900 g/mol to about 1,250 g/mol and wherein the relative content of said soft segment is about 60 to about 75 parts by weight whereas the relative content of said hard segment is about 40 to about 25 parts by weight.

5. The device according to claim 1, wherein said tubular sheath has a Young elasticity modulus of about 0.4 to about 2.5 MPa and a strain at break of about 200 to about 1000%.

6. The device according to claim 1, wherein said tubular sheath is of substantially frustoconical shape.

7. The device according to claim 1, wherein said second fibers are heterogeneous filaments having included cavities filled with said therapeutic agent.

8. The device according to claim 1, wherein said second fibers are hollow filaments having a central core filled with said therapeutic agent.

9. The device according to claim 1, wherein said first tubular region and said second tubular region each form about one half of the sheath's wall thickness.

10. The device according to claim 1, wherein said therapeutic agent is selected from the group consisting of growth hormones, pharmaceutical agents and growth promoting cells.

11. The device according to claim 10, wherein said therapeutic agent is platelet-derived growth factor—BB.

12. A method of producing a device according to claim 1, wherein said elastic fibers are formed by solution electrospinning.

13. The device of claim 1, wherein the device is adapted for the repair of a ruptured tendon.

14. The device of claim 10, wherein the growth promoting cells are stem cells.

15. Method for repairing surgery of cylindrical organs comprising providing the device of claim 1,
pulling the device over a wound site,
wherein the therapeutic agent stimulates the regrowth processes of the predetermined cylindrical organ.

16. The method of claim 14, wherein the cylindrical organ is a tendon.

* * * * *